US012285547B2

(12) United States Patent
Landon et al.

(10) Patent No.: US 12,285,547 B2
(45) Date of Patent: Apr. 29, 2025

(54) CONTROLLED RANDOMIZED POROUS STRUCTURES AND METHODS FOR MAKING SAME

(71) Applicant: Smith & Nephew, Inc., Memphis, TN (US)

(72) Inventors: Ryan L. Landon, Memphis, TN (US); Aashiish Agnihotri, Memphis, TN (US); Laura J. Gilmour, Memphis, TN (US); Jeffrey Sharp, Memphis, TN (US); Randy C. Winebarger, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 17/374,083

(22) Filed: Jul. 13, 2021

(65) Prior Publication Data

US 2021/0338901 A1 Nov. 4, 2021

Related U.S. Application Data

(60) Continuation of application No. 16/728,668, filed on Dec. 27, 2019, now abandoned, which is a
(Continued)

(51) Int. Cl.
B22F 10/85 (2021.01)
A61L 27/56 (2006.01)
(Continued)

(52) U.S. Cl.
CPC ............. A61L 27/56 (2013.01); B22F 10/85 (2021.01); B33Y 50/00 (2014.12); G06F 30/10 (2020.01); A61L 27/30 (2013.01); A61L 2420/02 (2013.01); A61L 2430/02 (2013.01); B33Y 80/00 (2014.12); Y10T 428/249953 (2015.04)

(58) Field of Classification Search
CPC ...................................................... B22F 10/85
See application file for complete search history.

(56) References Cited

U.S. PATENT DOCUMENTS 5,639,402 A 6/1997 Barlow et al.
5,869,170 A 2/1999 Cima et al.
(Continued)

FOREIGN PATENT DOCUMENTS

EP 1683593 A2 7/2006
JP 2003-513879 A 4/2003
(Continued)

OTHER PUBLICATIONS

Indian Office Action; Intellectual Property India; Indian Patent Application No. 3985/DELNP/2012; 6 pages.
(Continued)

Primary Examiner — Christopher S Kessler
(74) Attorney, Agent, or Firm — KDW Firm PLLC

(57) ABSTRACT

Improved randomized porous structures and methods of manufacturing such porous structures are disclosed. The scaffold of the porous structures are formed from by dividing the space between a plurality of spatial coordinates of a defined volume, where the plurality of spatial coordinates have been moved in a random direction and a random finite distance according to a predetermined randomization limit.

19 Claims, 23 Drawing Sheets

Related U.S. Application Data continuation of application No. 16/153,207, filed on Oct. 5, 2018, now abandoned, which is a division of application No. 13/509,585, filed as application No. PCT/US2010/056602 on Nov. 12, 2010, now Pat. No. 10,166,316.

(60) Provisional application No. 61/260,811, filed on Nov. 12, 2009.

(51) Int. Cl.
    *B33Y 50/00*     (2015.01)
    *G06F 30/10*     (2020.01)
    *A61L 27/30*     (2006.01)
    *B33Y 80/00*     (2015.01)

(56) References Cited

U.S. PATENT DOCUMENTS

| | | |
|---|---|---|
| 6,582,715 B1 | 6/2003 | Barry et al. |
| 6,932,610 B2 | 8/2005 | Ono et al. |
| 2003/0220696 A1 | 11/2003 | Levine et al. |
| 2004/0009228 A1 | 1/2004 | Tormala et al. |
| 2004/0191106 A1 | 9/2004 | O'Neill et al. |
| 2005/0079200 A1 | 4/2005 | Rathenow et al. |
| 2006/0147332 A1 | 7/2006 | Jones et al. |

FOREIGN PATENT DOCUMENTS

| | | |
|---|---|---|
| JP | 2016-120322 A | 7/2016 |
| WO | 2001036013 A1 | 5/2001 |

OTHER PUBLICATIONS

Japanese Office Action with English Translation, Japanese Patent Office; Japanese Patent Application No. 2016-029928; Sep. 21, 2018;14 pages.

Japanese Office Action with English Translation; Japanese Patent Office; Japanese Patent Application No. 2017-213875; Aug. 27, 2018; 6 pages.

Guibas, et al., "Randomized incremental construction of Delaunay and Voronoi diagrams," Algorithmica (1992) 7:381-413.

European Office Action; European Patent Office; European Patent Application No. 10830822.2; Aug. 22, 2014; 6 pages.

Cheah et al., "Automatic Algorithm for Generating Complex Polyhedral Scaffold Structures for Tissue Engineering", Tissue Engineering, vol. 10, No. 3/4, 2004, pp. 595-613, Copyright Mary Ann Liebert, Inc.

Interview Summary and Final Office Action from U.S. Appl. No. 11/027,421, dated Nov. 16, 2009.

Amended claims from U.S. Appl. No. 11/027,421, filed Jun. 22, 2009.

Borovinsek, M. and Ren, Z. (2008), Computational modelling of irregular open-cell foam behaviour under impact loading. Mat.-wiss. u. Werkstofftech., 39: 114-120. Abstract only.

International Search Report and Written Opinion issued for PCT/US2010/056602, dated Jul. 28, 2011, 9 pages.

Notice of Reasons for Rejection for Japanese Patent Application No. 2019-054635, mailed Mar. 9, 2020.

CONTROLLED RANDOMIZED POROUS STRUCTURES AND METHODS FOR MAKING SAME

CROSS-REFERENCE TO RELATED APPLICATIONS

This application is a continuation application of pending U.S. patent application Ser. No. 16/728,668, filed Dec. 27, 2019, entitled "Controlled Randomized Porous Structures and Methods for Making Same", which is a continuation application of pending U.S. patent application Ser. No. 16/153,207, filed Oct. 5, 2018, entitled "Controlled Randomized Porous Structures and Methods for Making Same", which is a divisional application of U.S. patent application Ser. No. 13/509,585, filed Aug. 7, 2012, now U.S. Pat. No. 10,166,316, entitled "Controlled Randomized Porous Structures and Methods for Making Same", which application is the national phase application under 35 U.S.C. 371 of International Application No. PCT/US2010/56602, filed Nov. 12, 2010, entitled "Controlled Randomized Porous Structures and Methods for Making Same", which claims priority to, and the benefit, of U.S. Provisional Patent Application No. 61/260,811, filed Nov. 12, 2009 and entitled "Controlled Randomization of Porous Structures for Medical Implants," the disclosures of which are incorporated by reference herein in their entirety.

FIELD OF THE DISCLOSURE

The present invention generally relates to porous structures suitable for medical implants, and more particularly to porous structures suitable for medical implants that have improved combinations of strength, porosity and connectivity and methods for fabricating such improved porous structures.

BACKGROUND OF THE DISCLOSURE

Certain medical implants and orthopedic implants require strength for weight bearing purposes and porosity to encourage bone/tissue in-growth. For example, many orthopedic implants include porous sections that provide a scaffold structure to encourage bone in-growth during healing and a weight bearing section intended to render the patient ambulatory more quickly. For example, metal foam structures are porous, three-dimensional structures that have been used in medical implants, particularly orthopedic implants, because they have the requisite strength for weight bearing purposes as well as the requisite porosity.

Metal foam structures and other porous structures can be fabricated by a variety of methods. For example, one such method is mixing a powdered metal with a pore-forming agent (PFA) and then pressing the mixture into the desired shape. The PFA is removed using heat in a "burn out" process. The remaining metal skeleton may then be sintered to form a porous metal foam structure.

Another similar conventional method includes applying a binder to polyurethane foam, applying metal powder to the binder, burning out the polyurethane foam and sintering the metal powder together to form a "green" part. Binder and metal powder are re-applied to the green part and the green part is re-sintered until the green part has the desired strut thickness and porosity. The green part is then machined to the final shape and re-sintered.

While metal foams formed by such conventional methods provide good porosity, they may not provide the desired strength to serve as weight bearing structures in many medical implants. Further, the processes used to form metal foams may lead to the formation of undesirable metal compounds in the metal foams by the reaction between the metal and the PFA. Conventional metal foam fabrication processes also consume substantial amounts of energy and may produce noxious fumes.

Rapid manufacturing technologies (RMT) such as direct metal fabrication (DMF) and solid free-form fabrication (SFF) have recently been used to produce metal foam used in medical implants or portions of medical implants. In general, RMT methods allow for structures to be built from 3-D CAD models. For example, DMF techniques produce three-dimensional structures one layer at a time from a powder which is solidified by irradiating a layer of the powder with an energy source such as a laser or an electron beam. The powder is fused, melted or sintered, by the application of the energy source, which is directed in raster-scan fashion to selected portions of the powder layer. After fusing a pattern in one power layer, an additional layer of powder is dispensed, and the process is repeated with fusion taking place between the layers, until the desired structure is complete.

Examples of metal powders reportedly used in such direct fabrication techniques include two-phase metal powders of the copper-tin, copper-solder and bronze-nickel systems. The metal structures formed by DMF may be relatively dense, for example, having densities of 70% to 80% of a corresponding molded metal structure, or conversely, may be relatively porous, with porosities approaching 80% or more.

While DMF can be used to provide dense structures strong enough to serve as weight bearing structures in medical implants, the porous structures conventionally used employ arrangements with uniform, non-random, and regular features that create weak areas where the struts of the three-dimensional porous structure intersect. That is, the conventional structure configurations lack directional strength and compensate for the weakness by making struts thicker, thereby decreasing the porosity, and conversely, a conventional structure with the desired porosity often lacks the desired strength because of the thinner struts. That is, the desired strength can be achieved in the prior art at the expense of porosity, or vice versa. There are no methods and/or products currently available that provide both the improved strength, improved porosity, and improved connectivity.

Further, trabecular bone structures are non-uniform and random in appearance on a micro-scale. It is also known that effective medical implants must be physiologically compatible with their surroundings in addition to providing the requisite strength, porosity and connectivity. Yet the conventional porous structures with uniform, non-random, and regular features that do not resemble trabecular bone structures. For example, U.S. Publication Nos. 2006/0147332 and 2010/0010638 show examples of these prior art configurations employed to form porous structures that exhibit the disadvantages discussed above, e.g., weak areas at the strut intersections, improved strength at the expense of porosity, and no trabecular features.

One way to enhance the effectiveness of an orthopedic implant may be to randomize the porous structure of an implant so it better simulates trabecular structures in which it is implanted. Therefore, in addition to strength, porosity and connectivity properties, it is believed that the performance of an implant with a porous structure could be improved if the porous structure could be randomized porous thereby providing a randomized scaffold structure as opposed to a uniform open cell structure. Methods known in the art to create randomized structures typically involve randomizing an existing uniform structure. These methods, however, are limited because they typically require manual manipulation of the struts, i.e., solid space, of one unit to match up with another unit to build a scaffold of desired dimensions. If the struts of the units do not match up, the integrity of the structure may be compromised if it has too many loose struts. Similarly, a randomized structure with poorly oriented struts may have poor distribution of residual stresses due to the manufacturing method resulting in warped or inaccurate parts. Accordingly, the structure of the initial units of the prior art, either identical or not, is usually simple to keep the stacking or building process manageable. Otherwise, building a scaffold from complex randomized initial units would be too time consuming and costly, particularly in computation expenses. Further, an additional drawback to randomizing an existing uniform structure is potentially making the structure weaker due to the unanticipated changes in the properties of the structure resulting from changes in the modulus and direction during the randomization process. Consequently, an original randomized structure, as opposed to a randomized existing structure, provides for improved strength along with improved porosity and enhanced complexity—e.g., trabecular features. As mentioned above, in the prior art, software applications typically produce porous structures that are predominantly uniform and regular. For efficiency, they repeat a small unit tile in the coordinate directions to fill a volume without gaps between the tiles. However, relatively few and simple shapes are employed within the unit tile due to the complexity of matching these tiles together.

Further, as a result of the deficiencies of metal foam implants and implants fabricated using conventional DMF methods, some medical implants require multiple structures, each designed for one or more different purposes. For example, because some medical implants require both a porous structure to promote bone and tissue in-growth and a weight bearing structure, a porous plug may be placed in a recess of a solid structure and the two structures may then be joined by sintering. Obviously, using a single structure would be preferable to using two distinct structures and sintering them together.

In light of the above, there is still a need for efficient methods to manufacture three dimensional porous structures, and the structures themselves, with randomized scaffold structures that provide for improved porosity without sacrificing the strength, improved strength including seamless junctions between units, and improved connectivity and having trabecular features.

SUMMARY OF THE DISCLOSURE

One objective of the invention is to provide porous biocompatible structures suitable for use as medical implants that have improved strength for weight bearing purposes and porosity for tissue in-growth structures.

Another objective of the invention is to provide porous biocompatible structures suitable for use as medical implants that have improved connectivity to resemble trabecular bone features.

Another objective of the invention is to provide porous biocompatible structures that promote bone tissue and soft tissue in-growth.

Another objective of the invention is to provide porous biocompatible structures suitable for use as medical implants having a controlled, yet random arrangement of struts and nodes for improved performance characteristics.

Yet another objective of the invention is to provide methods for fabricating such improved porous biocompatible structures.

Another objective of the invention is to provide efficient methods for fabricating randomized porous structures by manipulating the space between the struts.

Yet another objective of the invention is to provide methods for providing a seamless fit between structures that are joined together, regardless of whether the structures are identical or not.

Another objective of the invention is to provide methods to fabricate a randomized porous structure that can be customized to specific needs, e.g., a particular patient or application, having the appropriate distribution, pore size, porosity, and strength.

Another objective of the invention is to provide methods for controlling the randomization of a scaffold for a structure.

To meet the above objectives, there is provided, in accordance with one aspect of the invention, a method for fabricating a porous structure comprising the steps of: creating a model of a porous structure, the creating step includes defining a three dimensional space having an outer boundary and an inner volume, placing a plurality of outer spatial coordinates along the boundary, placing a plurality of inner spatial coordinates in the inner volume, moving one or more inner spatial coordinates a finite distance in a random direction, moving one or more outer spatial coordinates a finite distance in a random direction. The step of creating a model of a porous structure further includes dividing the volume of the three dimensional space evenly among the randomized outer and inner spatial coordinates, defining the boundary of one or more divided volume with one or more struts and one or more nodes, where each strut has a first end, a second end, and a continuous elongated body between the first and second ends for each strut, and each node is an intersection of at least two struts, and selecting a thickness and a shape for one or more struts. The method further includes the step of fabricating the porous structure according to the model by exposing fusible material to an energy source.

In accordance with another aspect of the invention, the method also includes a step of providing a second three dimensional space that is a duplicate of the first three dimensional space where the inner and outer coordinates have already been randomized.

In one embodiment, the moving of the inner spatial coordinates a finite distance in a random direction is performed within a preselected or predetermined randomization limit that avoids any overlap of the inner spatial coordinates. In another embodiment, the moving of the outer spatial coordinates a finite distance in a random direction is performed within a predetermined randomization limit so that the randomized outer spatial coordinates of one three dimensional space match or correspond to their respective outer spatial coordinates on a second substantially identical three dimensional space. Alternatively, the second three dimensional space is not substantially identical to the first three dimensional space.

In one embodiment, a Voronoi tessellation is applied to the randomized spatial coordinates and struts to remove redundant struts. In another embodiment, the method includes the step of fabricating the porous structure that comprises two or more substantially identical three dimensional spaces having randomized spatial coordinates and corresponding struts. In some embodiments where the overlap of inner and outer spatial coordinates after randomization or perturbation is not problematic, randomization limits may be avoided altogether or used sparingly.

In some embodiments, only selected inner and/or outer spatial coordinates are perturbed or randomized. In other embodiments all or substantially all inner and/or outer spatial coordinates are randomized or perturbed.

The perturbations or randomizations may be carried out for each inner and each outer spatial coordinate, or for some of the outer spatial coordinates and some of the inner spatial coordinates, or for some of the outer spatial coordinates and none of the inner spatial coordinates, or a little as one region of the outer spatial coordinates. A complete randomization of all spatial coordinates is not required.

In some embodiments, the predetermined randomization is configured to avoid at least one inner spatial coordinate from overlapping with at least one other inner spatial coordinate. In other embodiments, the method further includes selecting a predetermined randomization limit for at least one inner spatial coordinate, the selecting comprising the steps of: defining a volume around the at least one inner spatial coordinate, the volume is based at least on the proximity of one other surrounding inner spatial coordinate; and limiting the randomized movement of the at least one inner spatial coordinate to be within the defined volume.

Yet in other embodiments, the defined volume comprises a geometric shape selected from the group consisting of spheres, Archimedean shapes, Platonic shapes, polyhedrons, prisms, anti-prisms and combinations thereof. In some embodiments, at least one dimension of said defined volume has a radius of less than 50% the distance between said at least one inner spatial coordinate and other surrounding inner spatial coordinate.

In other embodiments, the matching is accomplished by moving at least two corresponding outer spatial coordinates the same finite distance and the same direction. In some embodiments, the three dimensional space comprises a geometric shape selected from a group consisting of space filling polyhedra, space-filling convex polyhedra with regular faces, and space-filling convex polyhedra with irregular faces.

Yet in other embodiments, the shape selected for the struts comprises a polygon. In some refinements, the shape selected for one strut differs from the shape of another strut, where the selected shape is configured to promote tissue ingrowth.

In some embodiments, the fabricating step further comprises selecting a material for fabricating the one or more struts from the group consisting of metal, ceramic, metal-ceramic (cermet), glass, glass-ceramic, polymer, composite and combinations thereof. In other embodiments, the method further comprises selecting a metallic material from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

According to another aspect of the invention, there is provided a porous structure comprising a plurality of struts, each strut comprises: a first end; a second end; and a continuous elongated body between said first and second ends, said body having a thickness and a length; and a plurality of nodes, each node comprises an intersection of at least two struts, where the plurality of struts and nodes formed from a model created by dividing the space between a plurality of spatial coordinates of a defined volume, said plurality of spatial coordinates having been moved in a random direction and a random finite distance according to a predetermined randomization limit.

In some embodiments, the predetermined randomization is configured to avoid at least one inner spatial coordinate from overlapping with at least one other inner spatial coordinate. In other embodiments, the dimension of said defined space surrounding said one or more spatial coordinates is based at least on the proximity of one other surrounding spatial coordinate. In some refinements, the other spatial coordinate is a nearest neighbor to the one or more spatial coordinates.

Yet in other embodiments, the defined space comprises a geometric shape selected from the group consisting of spheres, Archimedean shapes, Platonic shapes, polyhedrons, prisms, anti-prisms and combinations thereof. In other refinements, at least one dimension of said defined volume has a radius of less than 50% the distance between said one or more spatial coordinates and said one other surrounding spatial coordinate.

In some refinements, the three dimensional space comprises a geometric shape selected from a group consisting of space filling polyhedra, space-filling convex polyhedra with regular faces, and space-filling convex polyhedra with irregular faces.

In other embodiments, a Voronoi tessellation is applied to the randomized plurality of spatial coordinates to divide the space between all spatial coordinates. In some refinements, the shape for the cross sectional of said struts comprises a polygon. In some refinements, the shape selected for one strut differs from the shape of another strut, where the shape selected is configured to promote tissue ingrowth.

In some embodiments, the porous structure further includes a material selected from the group consisting of metal, ceramic, metal-ceramic (cermet), glass, glass-ceramic, polymer, composite and combinations thereof. In other refinements, the metallic material is selected from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

According to yet another aspect of the present invention, there is provided, a method for providing a seamless union between at least two scaffolds comprising the steps of: providing at least two three-dimensional spaces, each space having an outer boundary and an inner volume, providing a total volume having said at least two spaces; placing a plurality of spatial coordinates along the outer boundary of each of said three-dimensional space, placing a plurality of inner spatial coordinates in the inner volume, of each of said three-dimensional space; forming said scaffold by dividing the volume of the three dimensional space among the outer and inner spatial coordinates and defining the boundary of a portion of said divided volume with one or more struts, where each strut has a first end, a second end, and a continuous elongated body between the first and second ends for each strut, selecting at least one thickness and at least one shape for one or more struts; and fabricating a porous structure according to the scaffold with said one or more struts having at least one thickness and at least one shape by exposing fusible material to an energy source. In some embodiments, the method further includes moving at least one spatial coordinate from one of said plurality of outer spatial coordinates and said plurality of inner spatial coordinates; said movement configured to provide a scaffold having a seamless union between said at least two spaces.

According to yet another aspect of the invention, there is provided, a porous structure having a plurality of struts, each strut comprises: a first end; a second end; and a continuous elongated body between said first and second ends, said body having a thickness and a length; and a plurality of nodes, each node comprises an intersection of at least two struts, where the plurality of struts and nodes formed from a model created by dividing the space between a plurality of spatial coordinates of two or more defined volumes. In some embodiments, a Voronoi tessellation is applied to the spatial coordinates to divide the space.

Other advantages and features will be apparent from the following detailed description when read in conjunction with the attached drawings. The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed methods and apparatuses, reference should be made to the embodiments illustrated in greater detail in the accompanying drawings, wherein.

Figure 1:
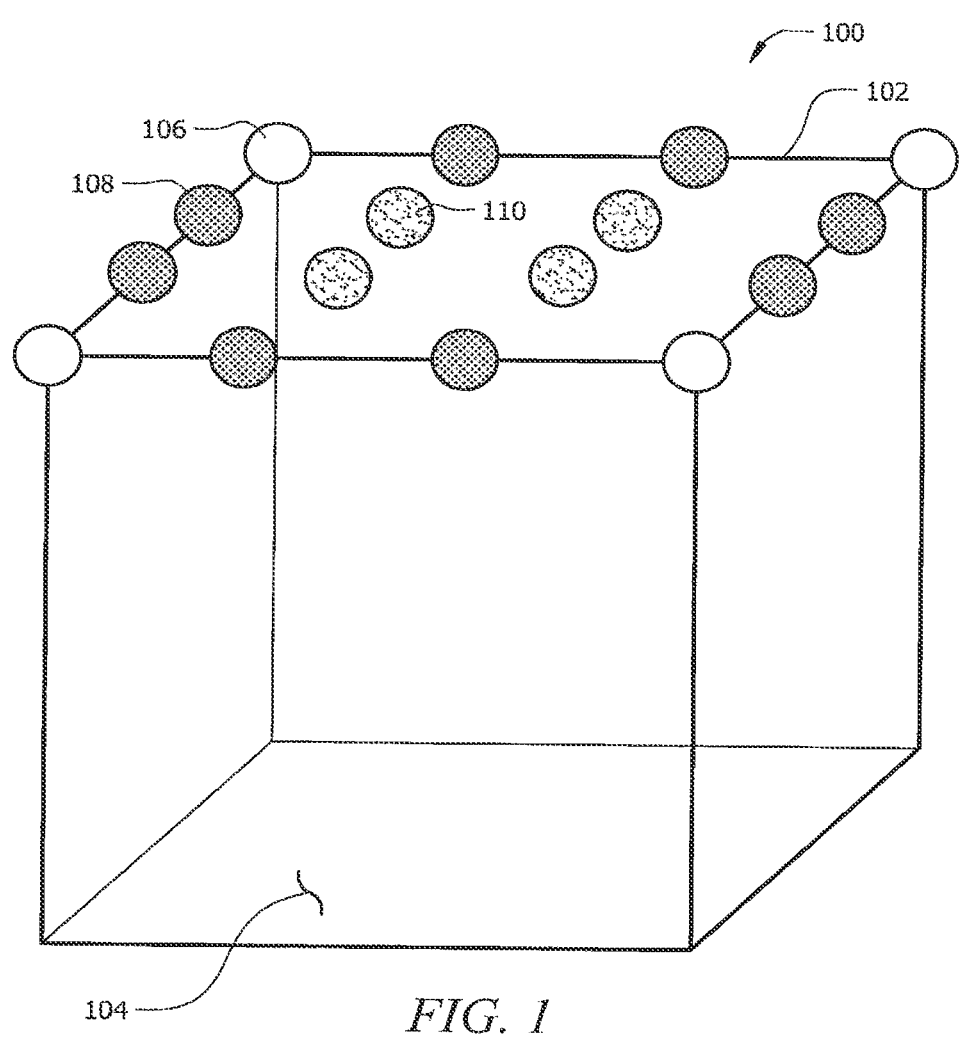
FIG. 1 is a perspective view of the initial cube volume illustrating a portion of the outer seed points or outer spatial coordinates according to one aspect of the present invention.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

The present disclosure provides for methods to fabricate porous structures with improved strength, porosity, and connectivity. Preferably, the improved porous structures of the present invention is formed by using a free-from fabrication method, including rapid manufacturing techniques (RMT) such as direct metal fabrication (DMF). Typically, in RMT or free-form fabrication, a model, or calculations defining the desired structure, or a computer readable file of the desired structure is provided to a computer-aided machine or apparatus that has an energy source such as a laser beam to melt or sinter powder to build the structure one layer at a time according to the provided model.

For example, RMT is an additive fabrication technique for manufacturing objects by sequential delivering energy and/or material to specified points in space to produce that part. Particularly, the objects can be produced in a layer-wise fashion from laser-fusible powders that are dispensed one layer at a time. The powder is fused, melted, remelted, or sintered, by application of the laser energy that is directed in raster-scan fashion to portions of the powder layer corresponding to a cross section of the object. After fusing the powder on one particular layer, an additional layer of powder is dispensed, and the process is repeated until the object is completed.

Detailed descriptions of selective laser sintering technology may be found in U.S. Pat. Nos. 4,863,538; 5,017,753; 5,076,869; and 4,944,817, the disclosures of which are incorporated by reference herein in their entirety. Current practice is to control the manufacturing process by computer using a mathematical model created with the aid of a computer. Consequently, RMT such as selective laser re-melting and sintering technologies have enabled the direct manufacture of solid or 3-D structures of high resolution and dimensional accuracy from a variety of materials.

In one embodiment of the present invention, the porous structure is formed from powder that is selected from the group consisting of metal, ceramic, metal-ceramic (cermet), glass, glass-ceramic, polymer, composite and combinations thereof. In another embodiment, metallic powder is used and is selected from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

In another embodiment, the disclosed fabrication methods may form a complete orthopedic implant structure, or the disclosed techniques may be applied to a substrate or work piece which forms part of an implant. The fabrication methods disclosed herein produce porous structures the desired porosity, pore size, strength and connectivity by controlling the randomization of the scaffold of a porous structure. Cell attachment, bone in-growth and initial fixation may be improved with the randomized scaffold structures produced by the disclosed methods because the scaffold structures better simulate natural trabecular structures. As an added benefit, the implants are more aesthetically pleasing to the physician and patient, since they better resemble natural trabecular structures.

Preferably, the randomized scaffold can be created by dividing a defined volume evenly between a series of seed points that have been randomized at the boundary and within the volume. The seed points have been randomized according to a predetermined randomization limit that is preferably designed to avoid any overlap of the seed points within the volume. If more than one identical volume is used to create the randomized scaffold, the predetermined randomization limit can be used to ensure the seed points at the boundary of the volume ("outer seed points") match up with the outer seed points of other identical volumes. As described, the volume has been divided into random portions because the seed points have been randomly placed, but the random division is controlled because there was a limit on the random placement of the seed points. The border of the divided portions serve as the struts of the randomized scaffold, and the randomized scaffold can be built into a porous structure once a strut thickness and shape are selected.

Figure 2:
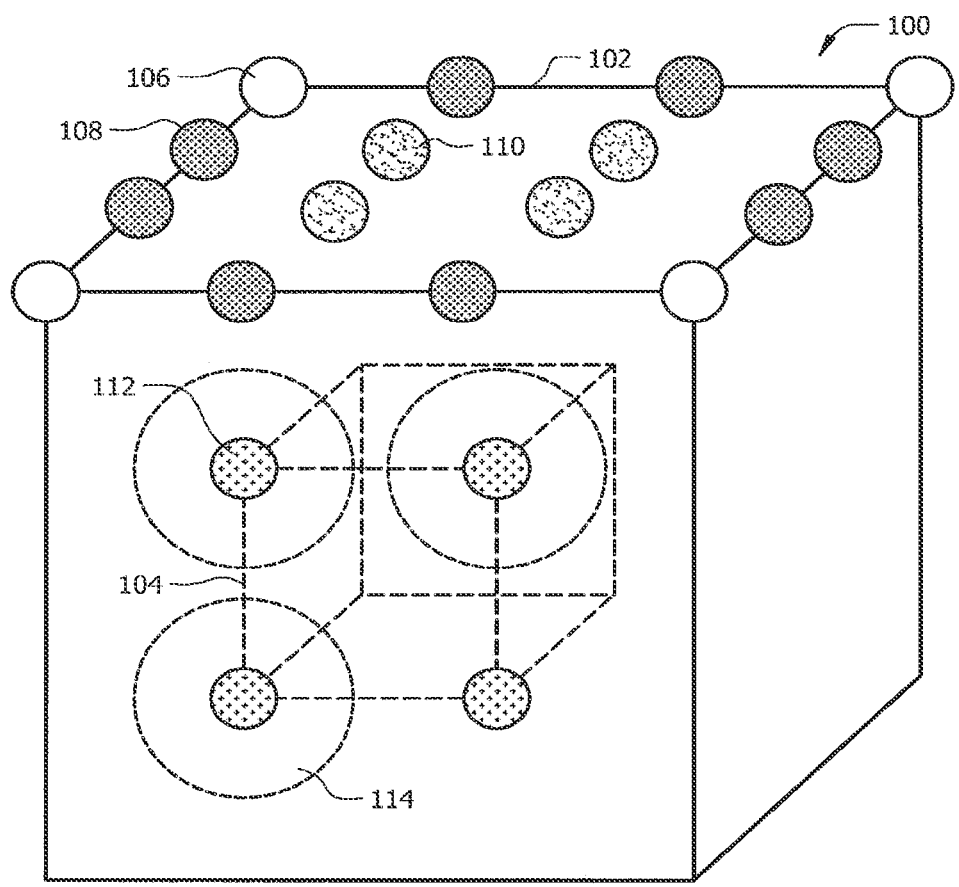
FIG. 2 is a perspective view of the initial cube volume of FIG. 1 with inner seed points according to one aspect of the present invention.

The following paragraphs provide more detailed descriptions and various embodiments and refinements of the present invention. Referring to FIGS. 1 and 2, an initial geometry in the form of a cube 100 may be chosen, which defines a volume. The cube 100 has an outer boundary 102 and an inner or interior volume 104. For demonstration purposes, FIG. 2 represents inner volume 104 as a cube within cube 100. This is not meant to limit the scope of the present disclosure where inner volume 104 can be any space within the outer boundary 102. In other embodiments, it is envisioned that other space-filling polyhedra can be used to define the disclosed volume. As illustrated, a plurality of outer seed points 106, 108, and 110 are placed at the outer boundary 102 of cube 100. While FIG. 1 shows only the top face of cube 100 containing these outer seed points, it is envisioned that in other embodiments, all or most of the faces of the cube or other space-filling polyhedra may contain these outer seed points. In FIG. 1, there are three types of outer seed points. The first type is the corner outer seed points 106, the second type is the edge outer seed points 108, and the third is the inbound outer seed points 110. In FIG. 1, These outer seed points are evenly distributed at the boundary of cube 100. Referring to FIG. 2, in addition to these outer seed points, a plurality of inner seed points 112 are placed in the inner volume 104. The number of seed points and their initial positions illustrated in these FIGS. is intended for illustration purposes only, and the actual number of inner and outer seed points depends on the initial spatial geometry and desired randomness. Also, in the preferred embodiment, the inner seed points are indexed and randomized independently of the indexing and randomization of the "outer" seed points. In other refinements, the randomization of the inner and outer seed points are not independent. For more complex inner seed point tiles or volumes, the copying or arraying process illustrated in FIG. 4 may need to be expanded beyond the seven-tile array shown in FIG. 4. Also, in some embodiments, the inner and outer seed points may be defined based at least upon the particular seed point's level of influence on the boundary between volumes. For instance, seed points that do not have any or have minimal influence on the boundary between volumes would be defined as inner seed points. On the other hand, seed points that have substantial influence on the boundary would be defined as outer seed points. Further, in these embodiments, it may not be necessary to array the inner seed point tiles or volumes as the inner seed points, as defined, should not have any influence or minimally influence the boundary.

Figure 3:
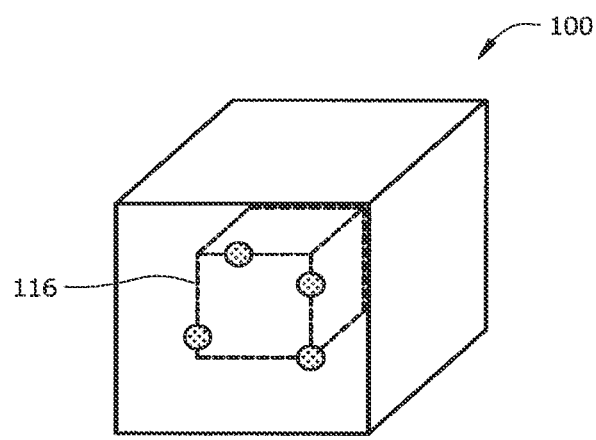
FIG. 3 is a perspective view illustrating a randomization of the inner seed points or spatial coordinates according to one aspect of the present invention.

After the inner seed points 112 are placed or created, their positions are randomized in three-dimensional space as illustrated in FIG. 3. Each seed point or spatial coordinate 112 is moved or "perturbed" in random directions by random magnitudes using a random number generator algorithm. That is, each seed point or spatial coordinate 112 is moved a finite distance in a random direction within cube 100, where the finite distance each seed point has been moved is also random. The perturbation or moving of the seed points 112 is not completely random, however, because a preselected or predetermined randomization limit is imposed on the random movement of each seed point 112.

In one embodiment, the predetermined randomization limit is based upon the position of the closest neighboring seed point 112, which can be determined by, for instance, the nearest neighbor algorithm or other similar algorithms. The limit ensures that the random movements of the inner seed points 112 do not cause one inner seed point to overlap with another inner seed point 112. One seed point can overlap another seed point by partially or fully lying on top of the other seed point, or there can also be overlap when one seed point enters the defined volume surrounding another seed point. Typically, overlapping occurs more or most frequently when two dissimilar tiles are joined together because the more dissimilar the tiles, the more difficult it is to distinguish inner and outer seed points. Conversely, overlapping occurs less frequently when substantially similar tiles are combined. One way of ensuring no overlap is to limit the movement of any inner seed point 112 to be within a volume determined by the proximity of surrounding inner seed points 112. In one embodiment, such a volume may be defined as a hexahedron or a sphere with at least one of its dimensions having a radius of less than 50% or half the distance to the closest neighboring seed point. For example, referring to FIG. 2, using the inner seed point 112a located at the lower left corner of the inner volume 104 as an example, the closest neighboring seed points to inner seed point 112a are inner seed points 112b and 112c. If the randomization of the inner seed point 112a is limited in magnitude or distance to within the volume of the sphere 114 surrounding point 112a, then the random placement of inner seed point 112a can only occur within that volume 114 and any random movements of point 112a cannot result in an overlap of point 112a with the other two seed points 112b and 112c.

In other embodiments, more abstract and complex volumes may be defined to delineate the bounds of perturbation for a given seed point. In yet other embodiments, different volume sizes can be used to limit the randomization. For instance, a 10% randomization limit placed on the movements of the inner seed points 112 means that each seed point 112 can be moved randomly within a sphere (or other shapes) having a radius of 10% of the distance between that particular seed point and its closest neighboring seed point prior to the perturbation. A 30% randomization limit means that each seed point can be moved randomly within a sphere having a radius of 30% of the distance between the seed point and its closest neighbor prior to perturbation. Accordingly, by limiting the random magnitude and direction of the perturbation of each inner seed point 112 to within a sphere or other defined three dimensional space 114 with a radius of less than half the distance to a neighboring seed point, the two seed points 112a and 112c cannot not overlap or engage each other even if the randomization results in these seed points moving directly toward each other. In some embodiments, greater limits of randomization may be established in order to allow seed point overlaps and seed point crossings during perturbation steps. However, by preventing seed points from overlapping and/or crossing, a higher level of porosity control and strength may be achieved. Accordingly, the randomization limit can be any number between 0% to 100% of the distance between a particular seed point and its closest neighbor, e.g., 5%, 10%, 15%, 20%, 25%, 30%, 35%, 40%, 45%, 50%, 55%, 60%, 65%, 70%, 75%, 80%, 85%, 90%, 95%, or 100%. In other embodiments, the range can exceed 100% the distance between a particular seed point and its closest neighbor. For instance, the range of the randomization limit can be 100% to 200% or 0% to 200%. Although the specification has discussed defining the predetermined randomization limit with respect to inner spatial coordinates, it should be understood that the steps discussed above can apply equally to randomizing outer spatial coordinates. In further embodiments, inner and outer seed points may be randomized using different methods and degrees of randomization.

Figure 4:
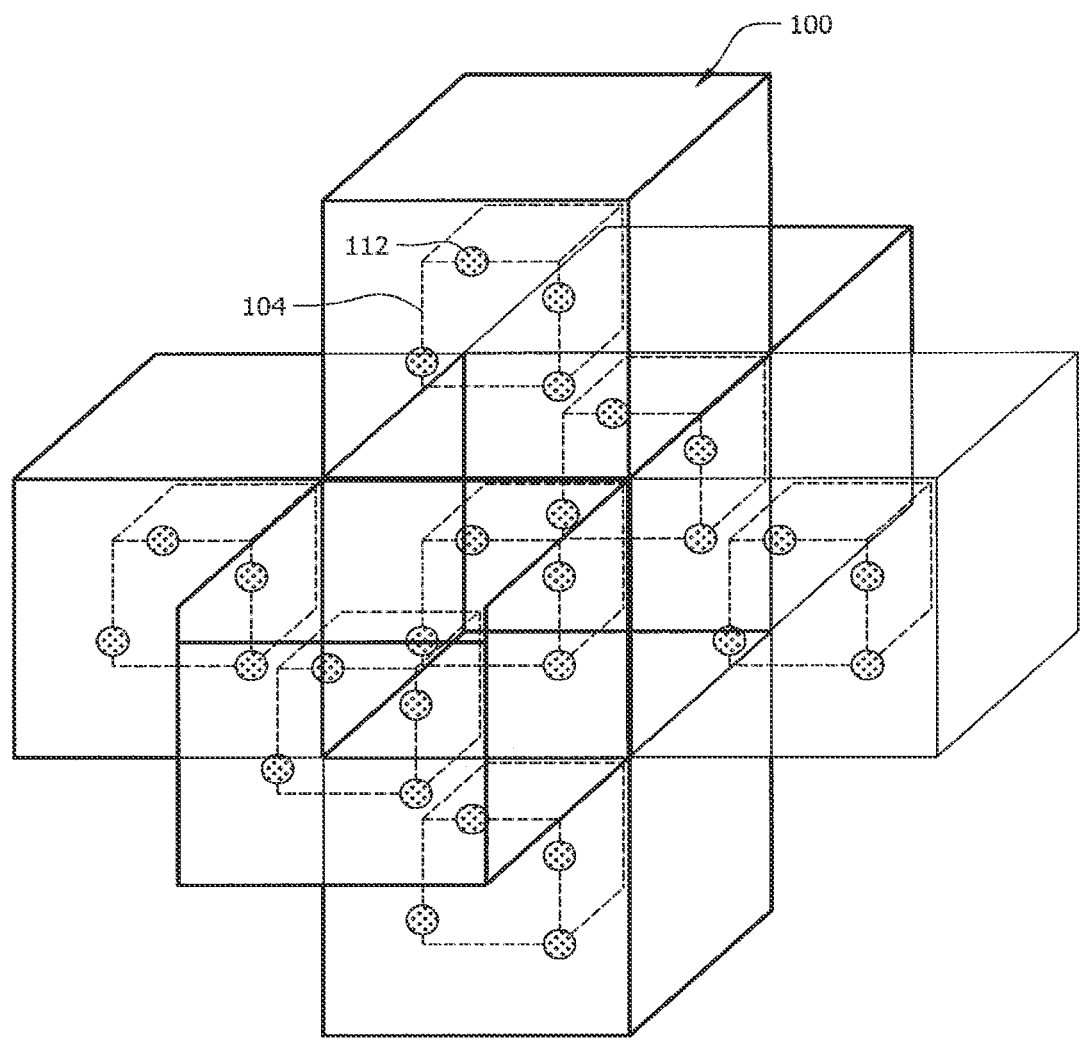
FIG. 4 is a perspective view illustrating one embodiment to confirm compatibility of the inner seed points according to one aspect of the present invention.

In the preferred embodiment, the model or randomized scaffold of the porous structure is created by arraying or stacking identical cloud volumes or tiles of perturbed seed points. When the duplicated cloud volumes or tiles are arrayed or stacked, it is preferred that the randomized inner seed points 112 do not intercept or create conflicts with the outer seed points 106, 108, and 110. One way of ensuring compatibility between the inner and outer seed points is to array identical versions of cube 100 with perturbed inner seed points 112 in three-dimensional space as illustrated in FIG. 4 where one of the six identical versions of cube 100 of FIG. 3 is placed adjacent to each face of cube 100 of FIG. 3.

Figure 5A:
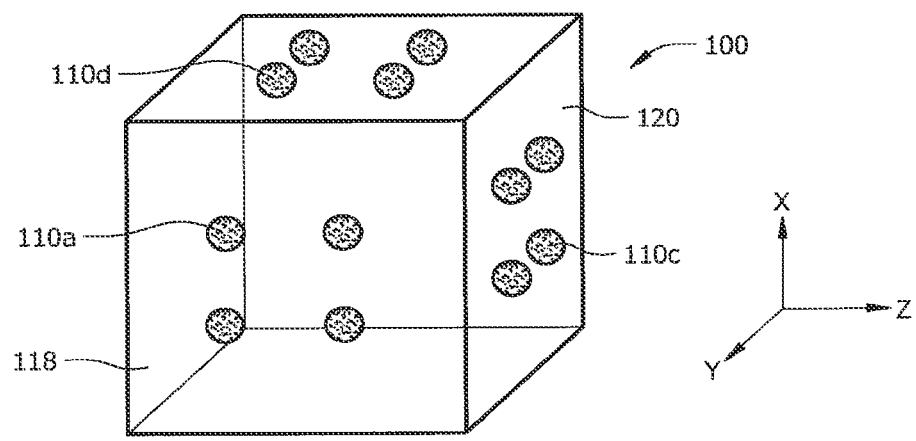
FIGS. 5A-5B are perspective views illustrating one embodiment to randomize certain outer seed points according to one aspect of the present invention.
Figure 6A:
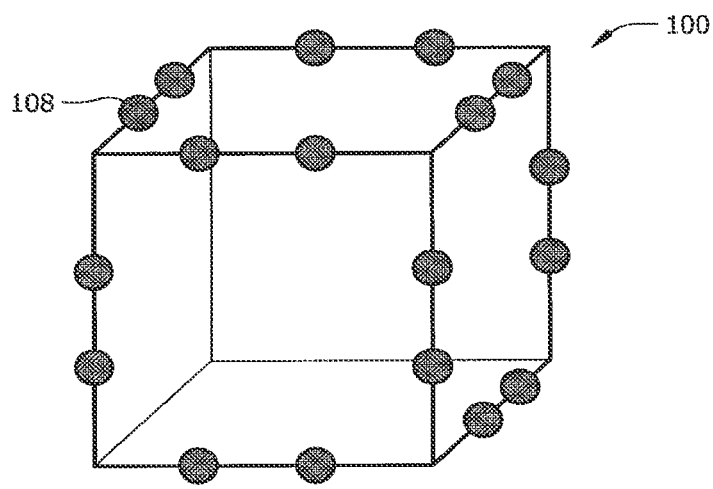
FIGS. 6A-6B are perspective views illustrating one embodiment to randomize other outer seed points according to one aspect of the present invention.
Figure 7A:
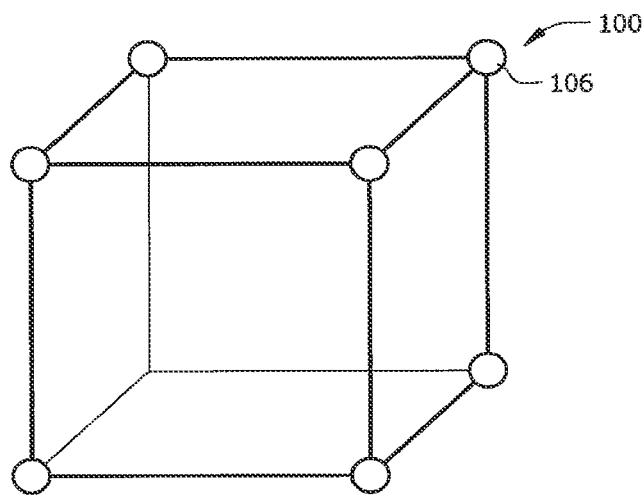
FIGS. 7A-7B are perspective views illustrating one embodiment to randomize yet other outer seed points according to one aspect of the present invention.

In a refinement, inner seed points 112 are randomized before the outer seed points 106, 108, and 110. Turning to FIGS. 5A-7A, the outer seed points 106, 108, and 110 are shown prior to perturbation. That is, FIG. 5A shows inbound outer seed points 110 evenly distributed on the top face, front face, and right side face of cube 100. FIG. 6A shows the edge outer seed points 108 evenly distributed around the edges of the top face, front face, and right side face of cube 100. FIG. 7A shows the corner outer seed points 106 evenly placed at the corners of the top face, front face, and right side face of cube 100. For simplification purposes, the outer seed points 106, 108, and 110 are shown only for the top face, front face, and right side face of cube 100. In other embodiments, more or less faces of the initial cube or other space-filling polyhedra can include these outer seed points. In the preferred embodiment, instead of randomizing the outer seed points 106, 108, and 110 together or as a group like the inner seed points 112, the outer seed points 106, 108, and 110 are randomized essentially in pairs due to the six-sided cubical geometry of cube 100. That is, each outer seed point and its counterpart outer seed points are identified and randomized in the same direction and magnitude.

Figure 5B:
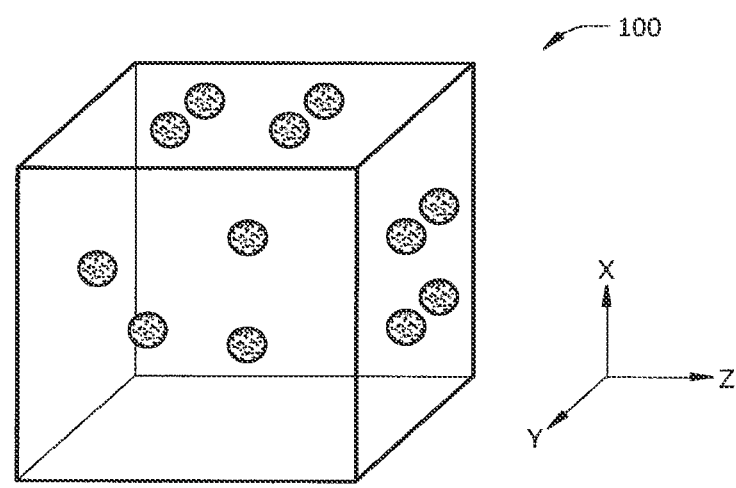
Figure 8:
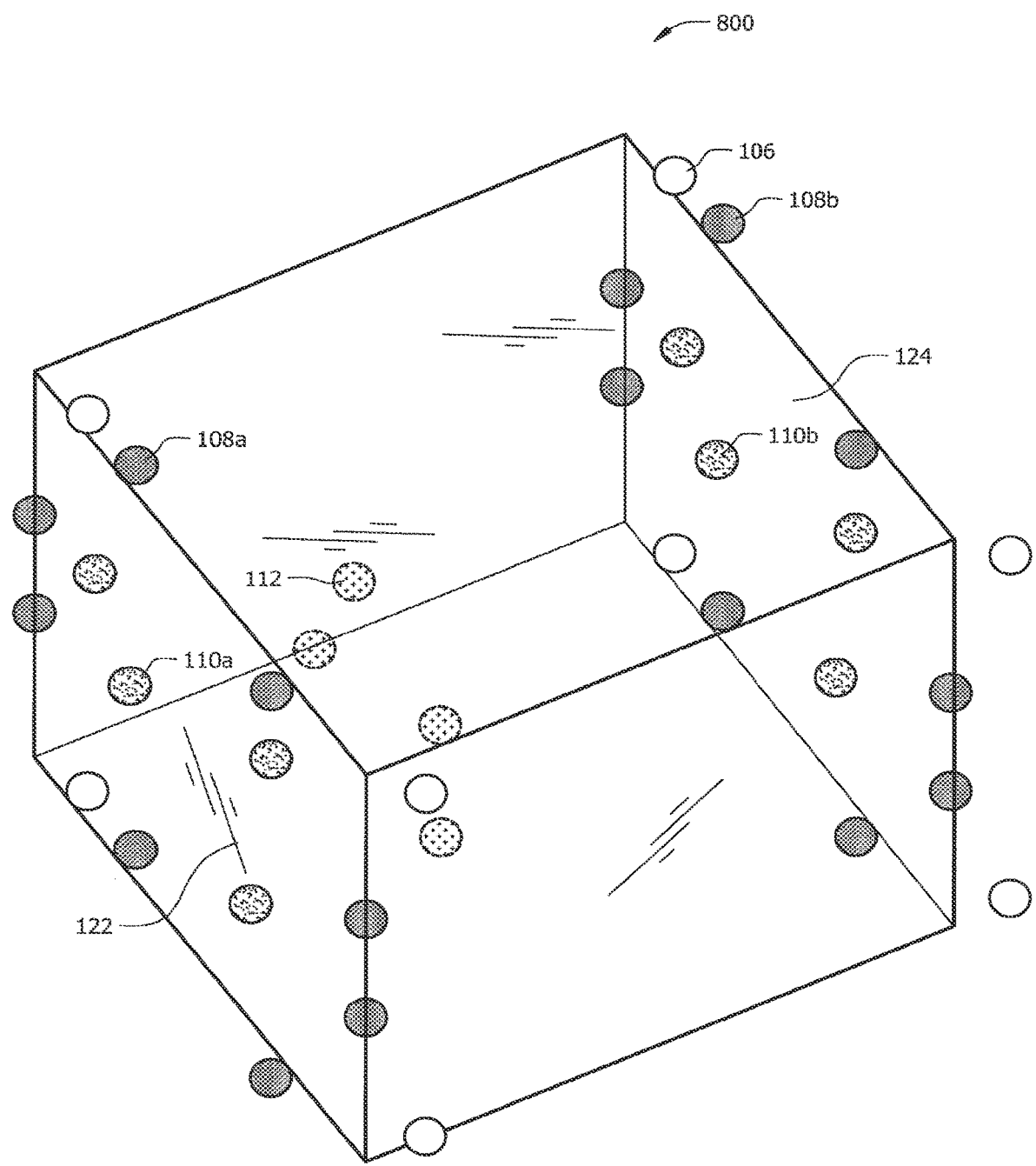
FIG. 8 illustrates one embodiment of a seed point cloud volume defined by randomized inner seed points and randomized outer seed points according to one aspect of the present invention.

Turning to FIGS. 5A and 5B, the outer seed points 110a of a front face region 118 are first identified and indexed. All the front outer seed points 110a may be randomized at the same time using the random number generator algorithm to generate the random finite distance and direction for each front outer seed point 110a, while the predetermined randomization limit (e.g., a sphere at 30% limit). Because the initial geometry 100 is a regular hexahedron, a corresponding set of outer seed points (not shown) on a back face region 120 are also identified, indexed, and randomized. Each back outer seed point (not shown) is randomized in the same direction and magnitude (distance) as its corresponding front outer seed point 110a. In other words, each front outer seed points 110a has identical x- and z-coordinates as its and its corresponding back outer seed point, but both have different y-coordinates. Each of the back outer seed points may be randomized individually or all the back outer seed points may be randomized as a group, so long as the randomization used for each back outer seed point is of the same magnitude and direction as its corresponding front outer seed point 110a. This process results in the front region 118 and the back face region 120 with identical randomized inbound outer seed points. The result is shown in FIG. 8, where the inbound outer seed points 110a of face 122 are identical in the x-direction and z-direction as the inbound outer seed points 110b of face 124. To confirm compatibility, the point clouds shown in FIG. 5B may be copied in three-dimensional space upwards, downwards and to all four sides in a similar manner as shown in FIG. 4.

For purposes of keeping FIGS. 5A and 5B simplified, the inbound outer seed points 110 on the top and side faces of cube 100 are not perturbed. Also, referring to FIG. 8, the faces, other than faces 122 and 124, of cube 100 are intentionally left blank. This, however, is only for demonstration purposes and does not limit the scope of either the claims or the present disclosure. That is, it is understood that the side outer seed points 110c can also be identified, indexed, and randomized as described for front face 118 and back face 120. That is the right side outer seed points 110c can be perturbed first according to a random number generator algorithm and a predetermined randomization limit, as described above. A corresponding set of left side outer seed points (not shown) are then randomized individually or as a group, where the magnitude and direction of each perturbation of the right outer seed points are identified and applied to each corresponding left outer seed points (not shown). Accordingly, the right and left outer seed points will have identical y- and z-coordinates, and different x-coordinates, after perturbation. To confirm compatibility, the resulting point clouds can be copied in three-dimensional space upwards, downwards and to all four sides in a similar manner as shown in FIG. 4. The same process can be performed for the top outer seed points 110d and corresponding bottom outer seed points. That is, after the top 110d and corresponding bottom outer seed points are identified, the corresponding pair of outer seed points are randomized using the same directions and magnitude to provide top and bottom outer seed points with identical x- and y-coordinates but different z-coordinates. The result is that the opposing top and bottom faces with identically randomized seed point clouds. To confirm compatibility, the resulting point clouds shown are copied in 3D space upwards, downwards and to all four sides in a similar manner as shown in FIG. 4.

In summary, inbound outer seed points disposed on, adjacent to, or defining a face region like seed points 110a, c, d in FIG. 5A, may be randomized as a group similar to the inner seed points 112; however, inbound outer seed points disposed along an opposite face region need to be moved in an identical fashion to their counterparts as shown and described above. In the embodiment shown in 5B, at least two of the six face regions will have matching inbound outer seed point patterns in space. In some embodiments, at least some seed points may be randomized, while other seed points remain unperturbed. For instance, some refinements may exist, where perturbations only occur at every Nth seed point in a region. Other refinements may include cubes or tiles or volumes of perturbed seed points, e.g., cube 800 of FIG. 8, where the one or more inner seed points 112 are perturbed while one or more outer seed points 106, 108, and 110 remain unperturbed and arranged in an ordered fashion to ensure compatibility between either randomized or non-randomized cubes or tiles or volumes.

It may be preferable to provide a gradient of randomness while still maintaining a controlled porosity and/or pore size. The gradient of randomness can be achieved by many means. One way is to gradually or abruptly increase the randomization limit (e.g., increasing from 10% to 30% limit) in one or more directions within a given cube or tile or volume. Another way is to gradually or abruptly increase the number of perturbed seed point in one or more directions within a cube or tile or volume. In yet other embodiments, only one or more outer seed point regions may be perturbed, and inner seed points 65 remain unperturbed to form a sandwich of non-random seed points between random seed points. More alternatively, some refinements may exist where seed points are only perturbed at predetermined regions within an overall seed point cloud cube or tile or volume, e.g., cube 800 of FIG. 8. Various combinations of the aforementioned embodiments are can be employed.

Figure 6B:
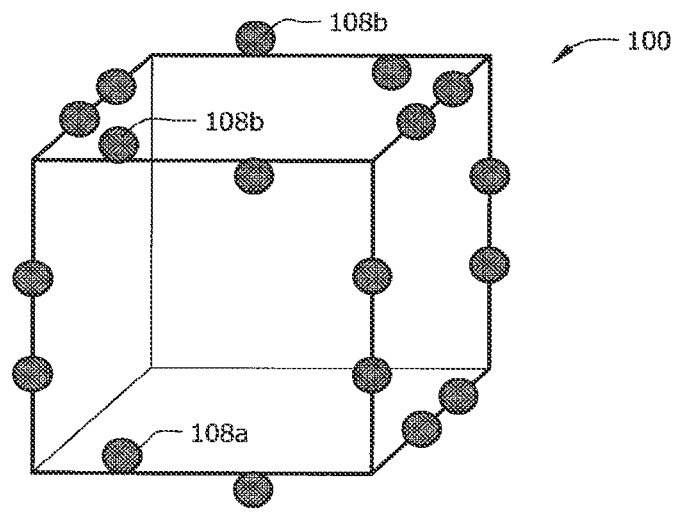

Turning to FIGS. 6A and 6B, a similar randomization process is employed for the edge outer seed points 108 disposed along the edge regions of cube 100. With embodiments employing regular hexahedron geometry (cube) as illustrated, seed points edge outer seed points 108 may be randomized in groups according to the following disclosure. FIG. 6A illustrates an even distribution of the edge outer seed points 108, which are disposed along the edge regions parallel with the x-axis, y-axis, and z-axis. In the preferred embodiment, all the edge outer seed points 108 are identified and randomized together as a group or individually. Regardless of individual or group randomization, the edge outer seed points 108 are perturbed with identical directions and magnitudes as shown in FIG. 6B. For purposes of keeping FIGS. 6A and 6B simplified, the edge outer seed points 108 of the back, bottom, and left faces of cube 100 are not shown, and only selected edge outer seed points 108 are perturbed. This, however, is only for demonstration purposes and does not limit the scope of either the claims or the present disclosure. To confirm compatibility, the point clouds shown in FIG. 6B can be copied in 3-D space upwards, downwards and to all four sides in a similar manner as shown in FIG. 4. In confirming compatibility, it is preferred that duplicated seed points are removed. In other embodiments, however, duplicated seed points may not be removed. In another embodiment, compatible seed point clouds may be reduced prior to any copying and/or arraying to prevent duplicate seed points during the multiplication process.

The perturbation process can be similarly repeated for other edge outer seed points 108. That is, other edge outer seed points 108 can also be identified, indexed, and randomized according to a random number generator algorithm and a predetermined randomization limit, as described above. A corresponding set of edge outer seed points (not shown) located at the opposite face of the cube is then randomized individually or as a group, where the magnitude and direction of each perturbation of the corresponding set of points are identical to the previously randomized set. Thus, for edge outer seed points 108 disposed along an edge region that is parallel to an axis, the seed points that share a common coordinate value for that axis can be randomized independently within the group or together, as long as their counter parts are randomized identically to ensure compatible edge regions. Here, unlike FIGS. 5A and 5B, perturbation of one edge outer seed point 108a results in the perturbation of three other corresponding edge outer seed points 108b (the third edge outer seed point is not shown). This is because two adjacent sides share one edge outer seed point 108. FIG. 8 demonstrates the identical randomization of corresponding sets of edge outer seed points 108 on faces 122 and 124. The other faces are left intentionally blank to keep FIG. 8 simplified. This, however, is not intended to limit the scope of the claims or present disclosure. It is envisioned that other edge seed points can be perturbed in the same manner and included in cube 800.

Figure 7B:
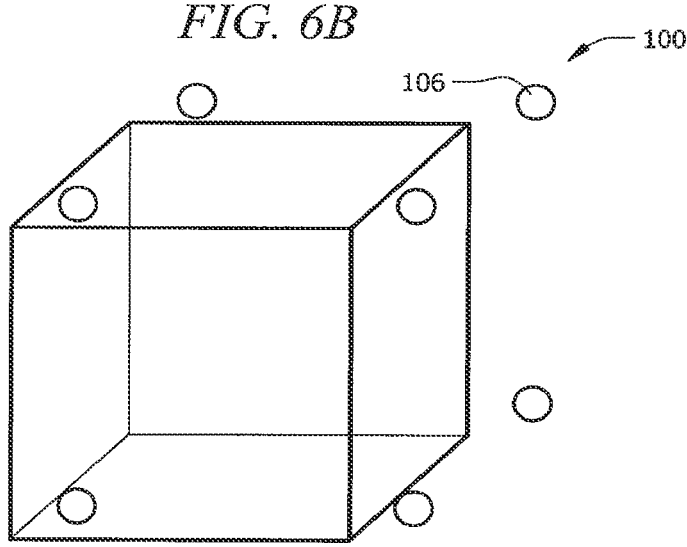

Turning to FIGS. 7A and 7B, for regular hexahedron geometry, the corner outer seed points 106 are identified and may be randomized together as a group but in an identical fashion as shown in FIG. 7B. In other words, each corner seed point 106 is moved in the same direction and by the same magnitude to ensure that all eight corner regions are compatible as illustrated in FIG. 7B. To confirm compatibility, the corner point clouds shown in FIG. 8A are copied in 3D space upwards, downwards and to all four sides in a similar manner as shown in FIG. 4.

Figure 9:
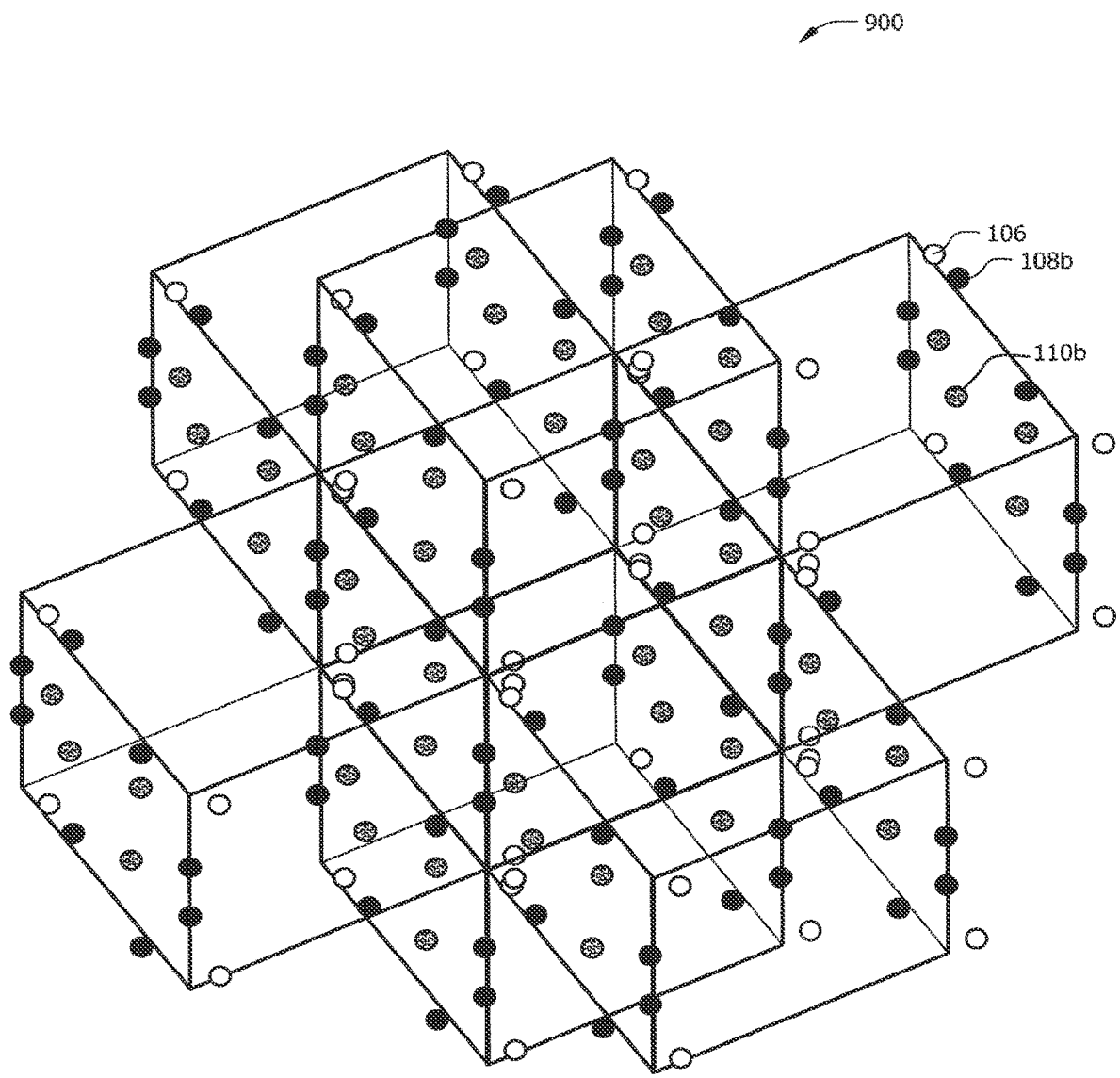
FIG. 9 illustrates one embodiment of an array of seven of the seed point cloud tiles illustrated in FIG. 8 according to one aspect of the present invention.

FIG. 8 demonstrates a resulting overall seed point cloud cube or volume 800 having an inner seed point cloud volume 104, and identical outer seed point clouds at face region 122 and face region 124, including identical edge, inbound, and corner outer points 106, 108, and 110. As mentioned above, only two faces of cube 800 are shown, but that is only for demonstration purposes and is not intended to limit the scope of the claims or the present disclosure. As already discussed, to ensure compatibility between the cubes, the seed point cloud volume 800 may be copied in three-dimensional space to the front, back, top, bottom and both sides to produce array 900 as illustrated in FIG. 9. To keep FIG. 9 simplified, inner seed point cloud volume 104 has been omitted. This, however, is not intended to limit the scope of the claims or the present disclosure.

In summary, after or during perturbation of the inner and outer seed points, to ensure that no unexpected aberrations occur at the boundaries or faces between the seed point cloud cubes or tiles or volumes, the randomized seed point cloud cube or tile or volume may be arrayed with identical seed point cloud tiles to make sure that: (1) the front and back face regions have matching seed point spatial patterns; (2) the right and left or side face regions have matching seed point spatial patterns; (3) the top and bottom face regions have matching seed point spatial patterns; (4) the edge regions disposed along and parallel to the x-axis have matching seed point spatial patterns; (5) the edge regions disposed along and parallel to the y-axis have matching seed point spatial patterns; (6) edge regions along and parallel to the z-axis have matching seed point spatial patterns; and (7) all corner regions have matching seed point spatial patterns. In one embodiment, an array of seed point cloud volume may be used for further processing to create the randomized scaffold of the porous structure. It should be noted that edge regions may not be parallel to a particular axis, especially for more complex shapes used for the initial geometry.

In a refinement, the randomization of the inner seed points 112 and the outer seed points 106,108, and 110 of the base cube or tile or volume is performed using a numerical computing environment algorithm. For example, the numerical computing environment algorithm may be a MATLAB™ algorithm. Other non-limiting examples of numerical computing environment programs SCILAB™, OCTAVE™, FREEMAT™, JMATHLIB™, MATHNIUM™, TELA™, ALGAE™, LUSH™, YORICK™, RLAB™, MAXIMAT™, SAGE™, EULER™, S-LANG LIBRARY™, PYTHON™, NUMPY™, SCIPY™, THE R PROJECT™, LUA™, any similar programs that provide the same or similar computing environments as the listed programs, and combinations, sub-combinations and variations thereof. Other programs will be apparent to those skilled in the art and future programs either under current development or future development will also be apparent to those skilled in the art. This disclosure is not limited to the particular software used to generate the randomized base tile and the software used to create three-dimensional structures from the multiplied randomized base cube or tile or volume. The volume of the initial geometry and number of seed points distributed within the volume and at the boundary can be chosen at the user's discretion. In the preferred embodiment, the volume and number of seed points depend on the information provided by clinical studies and literature regarding the preferred or optimal openings and pore size per volume.

While the figures illustrate the disclosed methods using a cubical space or cubical spatial coordinates, it will be noted here that this disclosure is not limited to six-sided base structures or six-sided outer geometries. Instead, as mentioned previously, the disclosed methods apply to any space filling polyhedra (sometimes referred to as plesiohedra), space-filling convex polyhedra with regular faces including the triangular prism, hexagonal prism, cube, truncated octahedron and gyrobifastigium, space-filling convex polyhedra with irregular faces including the rhombic dodecahedron, elongated dodecahedron, and squashed dodecahedron, and any non-self-intersecting quadrilateral prism. Other possibilities are too numerous to mention here. In lieu of Cartesian coordinates, spherical, cylindrical and other coordinates may also be used that would require the tiles to be appropriately scaled as they are positioned further away from the origin base tile. In a refinement, a gradient density algorithm can be incorporated into the data for the base tile to aid in matching up the borders between tiles. Thus, use of the terms "tile," "volume," and "initial geometry" herein covers multiple types of three-dimensional shapes.

In the preferred embodiment, the base volume of randomized seed points may then be multiplied and tiled together with other identical base volumes to form a three dimensional scaffold for a porous structure, where the scaffold has a controlled randomness. However, in other refinements, a single base volume of randomized seed points can serve as the scaffold for the porous structure. That is, if the initial volume selected is sufficiently large, then it can serve as the scaffold of a porous structure after seed points are planted and randomized in a controlled manner as described above. In this refinement, it may not be necessary to confirm compatibility with other identical volumes since only one volume is necessary to form the scaffold. The methods of the present disclosure are applicable to fabricate a variety of implants, including but not limited to, implants of the hip, including compression hip screws, knee, ankle, dental, shoulder, foot/hand, flanges, spine, skull plates, fracture plates, intramedullary rods, augments, staples, bone screws, cardiovascular implants, such as heart valves and artificial heart and ventricular assist devices, ligament and muscle fasteners, other small joint implants, and other implants. Also, while the base volume of randomized seed points is preferably used to build three dimensional scaffold structures for porous implants, it may apply to other applications as well, such as manufactured items that require resistance to vibrations, irregular loads, twisting of the structure, such as filters, heat sinks, cushions, wound dressings, cartilage or fat pad substitute, instrument weight reduction material, rasp, tissue sampling structure, debridement burr.

The disclosed techniques for fabricating porous structures of controlled randomness substantially reduce memory requirements of the RMT. For instance, the calculation for an initial tile or volume can be duplicated and reused to build an implant or many implants.

In embodiments using a plurality of identical volumes of randomized seed points produced by the process described above, it is also desirable to define an initial volume that is as large as possible so that the final scaffold has a minimal number of seams between tiles or volumes. If a spherical, cylindrical, etc. coordinate system is chosen, the tiles are scaled as they are positioned further and further away from the origin of the coordinate system or center of an array of seed points such as the one shown in FIG. 9. In that case, a gradient density within unit tiles may be used to aid in matching up the borders between tiles. The techniques for reducing memory and use of various software algorithms would still apply. The data can be exported to a RMT machine directly or exported to a machine or computer that controls the RMT machine.

Also in refinements of scaffolds using a plurality of identical volumes of randomized seed points, struts are then created for the scaffold by dividing the space between the randomized seed points with lines after compatibility between the identical cubes or tiles or volumes is confirmed. The division of the volume can be achieved in several ways. Preferably, it is done by applying any higher-order Voronoi tessellation algorithm, such as a QHull algorithm, Ken Clarkson's "Hull" algorithm, cdd, or Mac-Queen's k-means algorithm, to the randomized seed points. However, any method/algorithm of calculating the three-dimensional Voronoi tessellation, other than a QHull algorithm, may produce acceptable results. Because the compatibility between the identical cubes or tiles or volumes of randomized seed points has been confirmed, the Voronoi tessellation algorithm can be applied before or after the multiplication of the base volume of randomized seed points. That is, one way the scaffold can be built is by (1) creating a base volume of randomized seed points according to the disclosed methods, (2) multiplying and tiling a sufficient number of identical base volume of randomized seed points to form a scaffold with the desired dimensions, (3) dividing the space between all the randomized seed points generated by the copying and tiling of the base volumes, e.g., applying a higher order Voronoi tessellation algorithm, to form the struts of the scaffold, and (4) removing the seed points to form a three dimensional model of the randomized scaffold. A second way it can be done is by (1) creating a base volume of randomized seed points according to the disclosed methods, (2) dividing the space between the randomized seed points of just that single base volume of randomized seed points, e.g., applying a Voronoi tessellation algorithm, to form the struts for that base volume, (3) removing the seed points to form a base volume with randomized struts, and (4) multiplying the base volume with randomized struts and tiling a sufficient number of identical base volumes with randomized struts to form a scaffold with the desired dimensions. Both of these ways of dividing the space between the randomized seed points result in the same division and randomized struts structures for the scaffold. Also, before the space between the randomized seed points is divided, it is contemplated that certain seed points may be eliminated or additional seed points may be added to achieve the irregularity and/or porosity as desired or required by certain applications.

Figure 10:
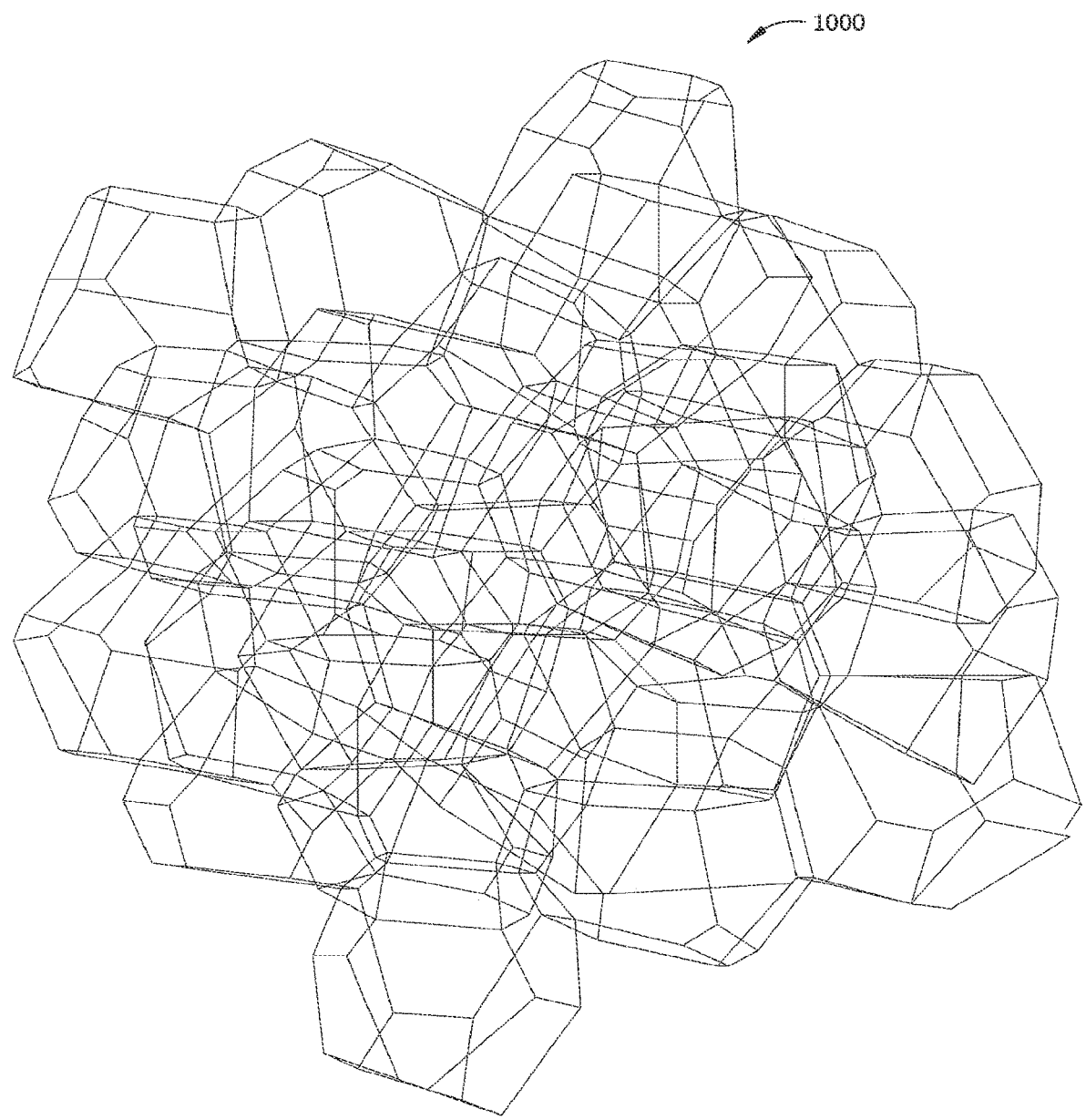
FIG. 10 illustrates one embodiment of a web or scaffold of randomized struts produced according to one embodiment of the present invention.

In one embodiment, a user can code the software program used to divide the space between the seed points to eliminate any redundant lines. FIG. 10 illustrates a base volume with randomized struts produced according to the present disclosure. That is, an initial geometry and volume were selected, inner and outer seed points were distributed according to the desired openings and pore size per volume, all or certain seed points were identified and randomized according to a predetermined randomization limit, the volume between the randomized seed points was divided according to an algorithm, e.g., Voronoi tessellation, and the seed points were removed to form tile or volume 1000 of FIG. 10. Volume 1000 of randomized struts can be tiled or stacked to form a scaffold for a porous structure of desired dimensions. After the size and thickness of the struts are selected, the scaffold model can be sent directly to the RMT machine to fabricate the porous structure.

Figure 11:
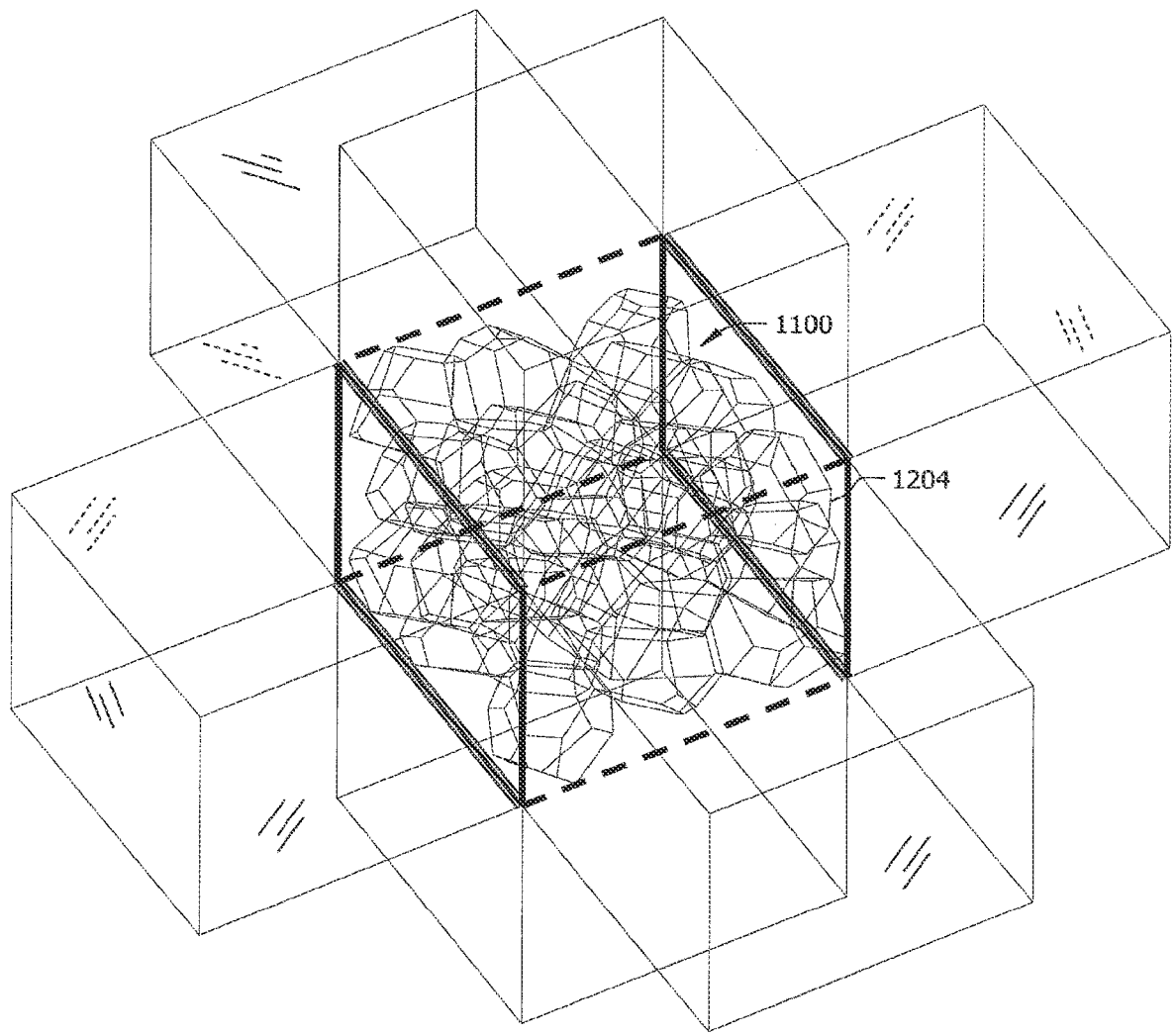
FIG. 11 illustrates the web or scaffold of randomized struts of FIG. 10 placed as the center tile in an array according to one aspect of the present invention.

In other embodiments, however, the step of dividing the space between the randomized seed points and eliminating any redundant lines may be separated. Referring to FIG. 11, the triangulated base volume or volume of randomized struts 1100 was produced by a different division of the space between the seed points where the division yielded various redundant lines or struts. FIG. also illustrates the spatial arrangement of the center tile to its coordinate neighbor tiles. The creation of redundant lines is typical of many Voronoi tessellations and/or QHull algorithms. If not eliminated, these redundant lines would result in unnecessary struts and nodes, which could consume unnecessary amounts of material and/or create various structural problems related to strength, porosity, connectivity, in the pore structure or incompatibilities between neighboring volumes with randomized struts.

Figure 12:
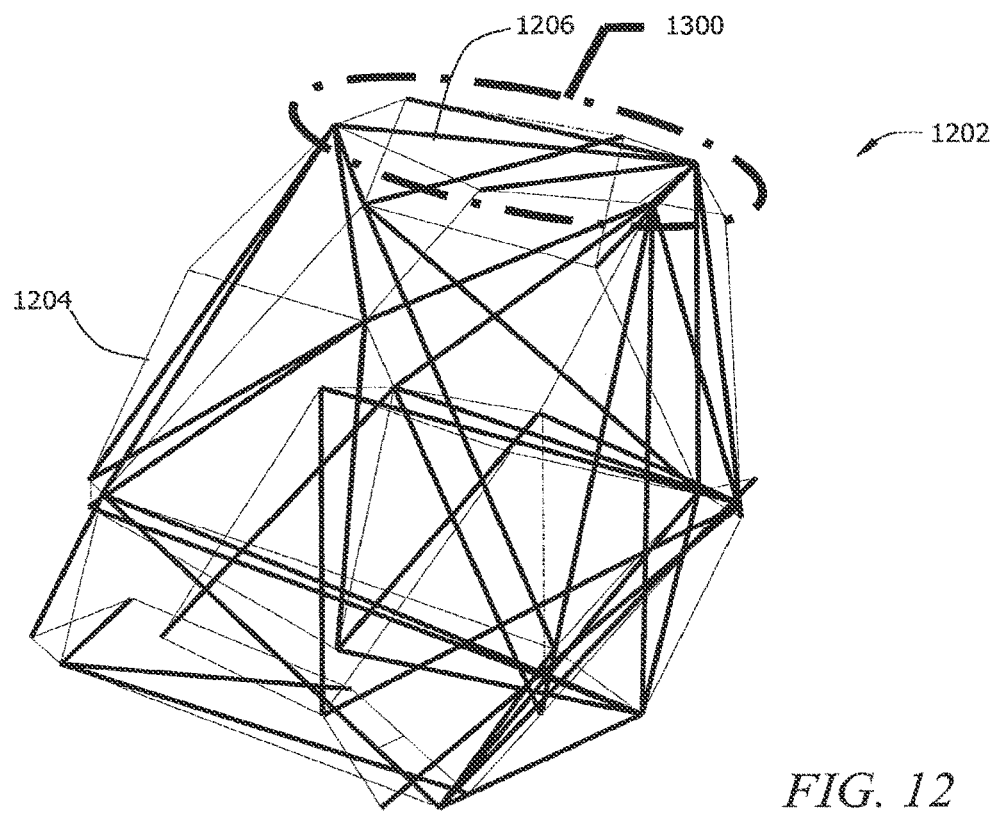
FIG. 12 illustrates the various lines of a convex hull according to one aspect of the present invention.
Figure 13:
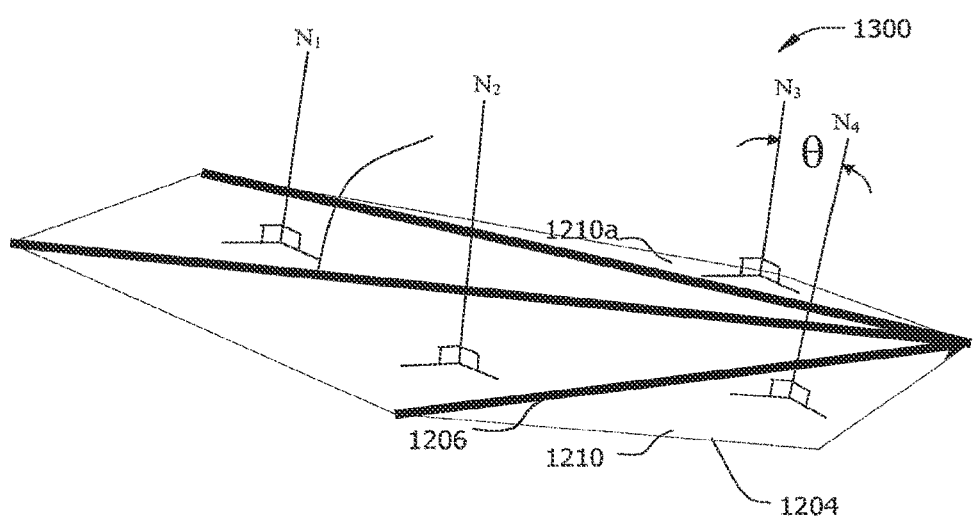
FIG. 13 illustrates one embodiment to remove certain redundant lines from the convex hull of FIG. 12 according to one aspect of the present invention.

One way of removing the excess redundant lines is illustrated in FIGS. 12-13. In FIG. 12, a convex hull 1202 is illustrated, where the convex hull 1202 is one of many that is part of the base volume 1100 of FIG. 11 before the redundant lines are removed. In FIG. 12, the structural lines 1204 of the convex hull 1202 are shown as thinner lines and the redundant lines 1206 of the convex hull 1202 are shown as thicker lines. FIG. 13 illustrates the treatment of one area 1300 of the convex hull 1202 to remove redundant lines 1206. Referring to FIG. 13, to eliminate or at least reduce the number of redundant lines 1206, a determination is made as to the extent which an alleged redundant line 1206 and/or a facet 1210 created by one or two redundant lines 1206 is co-planar with the surrounding structural face. Specifically, referring to FIG. 13, facets 1210 which may have redundant lines 1206 are identified. If an angle, between a line normal to a facet 1210, e.g., $N_4$, and a line normal to neighboring facet 1210, e.g., $N_3$, is sufficiently small or below a threshold angle θ, then the shared redundant line or redundant lines 1206 between facets could be eliminated. Similarly, if a line normal to the polygon face and a line normal to a facet 1210 is sufficiently small or below a threshold angle θ, then the interior redundant line or redundant lines 1206 may be eliminated. Other algorithms to eliminate redundant lines 1206 may be used. For instance, angles between lines can be compared with a threshold angle, and eliminated if they are less than the threshold angle. Alternatively, a shape recognition algorithm using polygon shape templates or polyhedral shape templates may be used to identify lines within the triangulated tile 1100 that collectively approximate the shape of the template. Structural lines 1204 not forming a portion of or falling within a tolerance of a shape template may be considered redundant lines 1206 and be removed.

The threshold angle θ is typically 10° or less, e.g., 1°, 2°, 3°, 4°, 5°, 6°, 7°, 8°, or 9°. If, after choosing a threshold angle θ that may be too low and some of the openings in a convex hull 1202 are still obscured by a number of redundant lines 1206, the threshold angle θ may be increased and the algorithm re-run. However, choosing a high threshold angle θ, e.g., greater than 10°, may risk of removing some of the desirable edges of a base volume with randomized struts. This is generally not desirable, but may advantageously be used to increase pore size without significantly affecting the strength. In another refinement, the threshold angle range may be less than 6°, and more preferably, the threshold angle range may be less than 4°.

Figure 14:
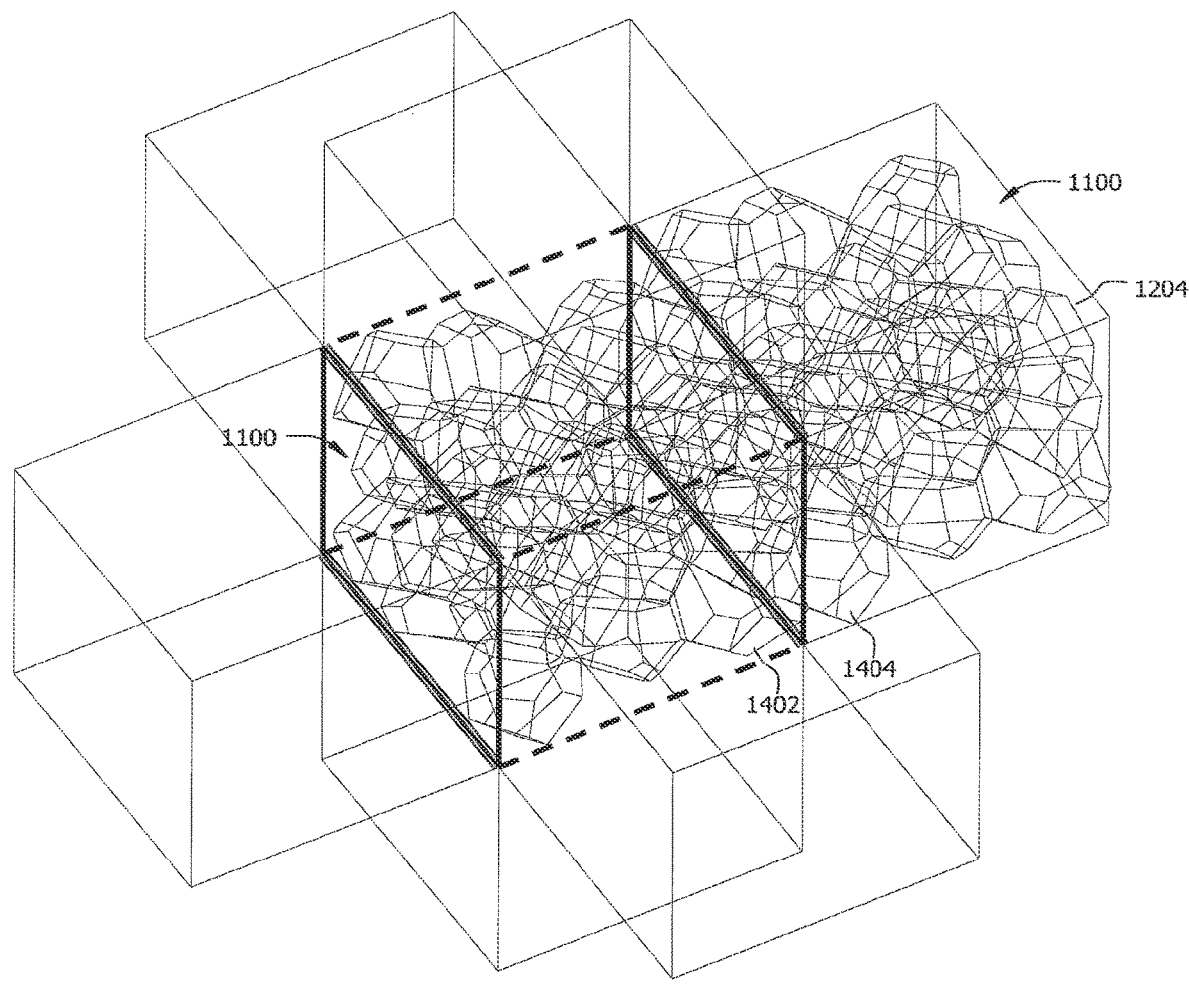
FIGS. 14-15 illustrate the seamless joining of two identical volumes of randomized struts disposed side-by-side according to one aspect of the present invention.
Figure 15:
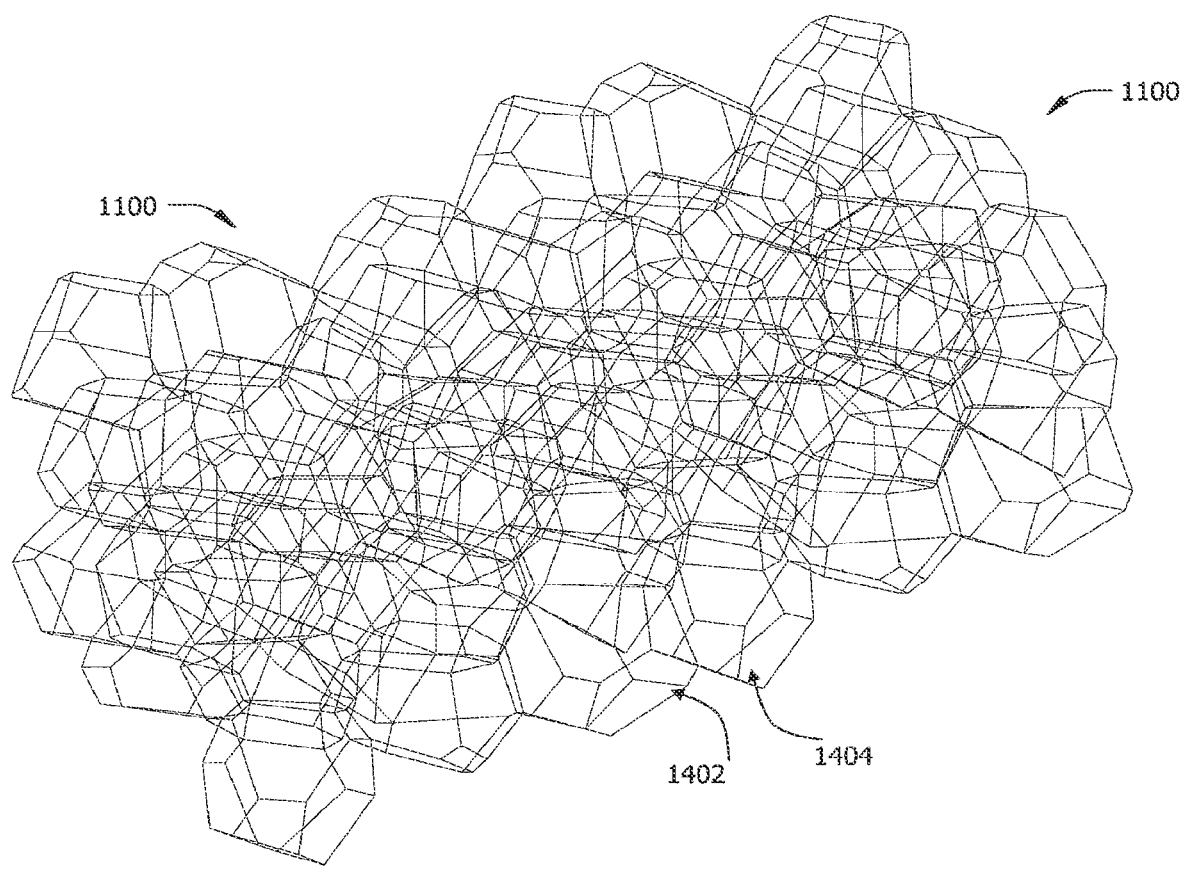

The above-described threshold angle θ limitation technique can also yield a base volume with randomized struts similar to base volume 1100 of FIG. 11. The base volume 1100 can be produced from the convex hull 1202 of FIG. 12 using a threshold angle θ of less than 10°. As shown in FIGS. 14-15, the resulting base volumes 1100 (whether produced by a one step Voronoi tessellation and redundant line removal or a two-step algorithms) fit together seamlessly with compatible faces 1502 and 1504. This is possible because the spatial coordinates (locating the voids) in close proximity to the compatible faces on each tile were placed in a compatible arrangement before the web or scaffold of struts for each tile was created. While the preferred embodiment provides for a porous structure where the redundant lines are removed to eliminate all loose struts, it is envisioned that other embodiments may have loose struts and are still in accordance with the present disclosure.

Figure 16:
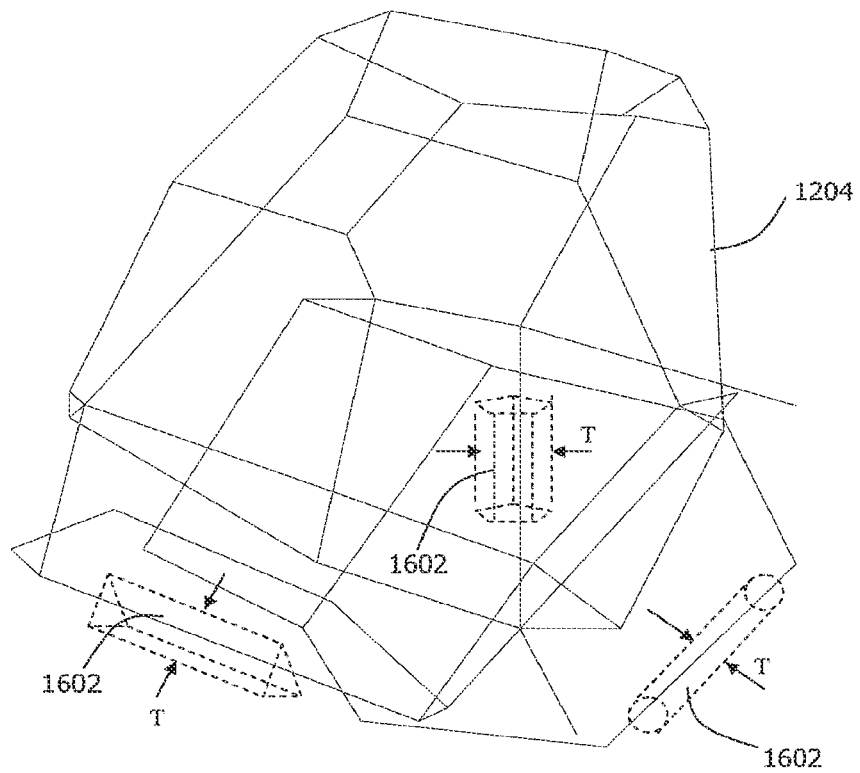
FIG. 16 illustrates one refinement to apply certain shapes and thicknesses to the struts of the volume of randomized struts in FIG. 11.

After a scaffold comprising one or more base volumes of randomized struts is created, the line data of that scaffold may be exported a modeling program or algorithm, or directly to rapid manufacturing equipment (e.g., by first converting line data to a *.stl file and downloading to a rapid prototyping machine). When the scaffold is sent directly to the machine, it must have a means of determining which portion of the scaffold should be built and which should be ignored because it is outside of the solid part. In one example, the lines defining the struts of base volume 1100 may be assigned a coordinate system, which can be used to transform individual STL shells representing an idealized strut of appropriate shape and thickness to the location of the lines. Then the resulting collection of STL shells is written to an STL file to define a porous three-dimensional tile. In another example, the lines defining the struts of base volume 1100 may be converted to a text file (*.exp extension) that corresponded to UNIGRAPHICS™ "expressions" that could be imported into such a modeling program. The solid-modeling program serves the purpose of taking a scaffold structure with infinitely thin lines, such as the base volume 1100 of FIG. 11 and provides the struts with appropriate shapes and thicknesses T. FIG. 16 demonstrates examples of the different geometric shapes 1602 and thicknesses T available for the struts 1204, e.g., circle, triangle, pentagon. The identified shapes are for demonstration purposes and are not intended to limit the scope of the claims or present invention. For example, other geometric shapes can include a square, rectangle, hexagon, octagon, heptagon, etc. In some embodiments, the strut thickness can be proportional to the length of the strut or the pore size. For instance, if the pores are bigger, they can accommodate larger struts and still maintain a desired pore opening size. Also, in instances where the struts are longer than a predetermined or selected length, they can be thickened to create more uniform strength characteristics with struts that are shorter as long struts are more flexible and/or weaker than shorter struts having the same thickness.

In other refinements, the three dimensional scaffold model may be converted to line data readable by a CAD program or directly to data readable by a solid modeling program if not already in a format directly readable by rapid manufacturing equipment. Other sold-modeling programs may be used or algorithms may be used to apply one or more predetermined thicknesses to the line data of the three dimensional scaffold model, so the model can be exported to the machine for fabricating a corresponding porous structure.

In one embodiment, during the modeling process, the strut lines 1204 (e.g., FIG. 11, 14, or 15) may be recorded in a part file, and then when reading in the lines 1204 using a modeling program and applying the desired thicknesses T, the struts 1204 may be oriented to match an adjacent tile or volume. The locations of each endpoint of each strut 1204 may be read as an ordered pair. The modeling program may also allow the diameter/thickness of strut 1204 and any other relevant information to be inputted, such as the general width, length, and height of the tile or volume 1100 (e.g., FIG. 11). Randomization algorithms similar to those described herein for perturbing seed points may also be used to randomly assign cross-sectional shapes or randomly assign strut thicknesses to one or more lines 1204 in any portion of the base volume of randomized struts 1100 of FIG. 11. Asymmetries or non-uniform profiles may be defined in a part file and then associated with one or more lines 1204 to form one or more struts within a tile or volume, e.g., volume 1100 of FIG. 11, that are non-uniform. Such associations may be random, selectively predetermined, or may be applied to every line within a base volume of randomized struts. Struts 1204 may also be randomly or non-randomly assigned a taper angle or a varying cross-sectional shape from one endpoint to another endpoint. Providing different shapes and/or dimensions to each strut as described may provide better strength, biologic fixation, and trabecular appearance, while maintaining full control of overall porosity.

Figure 17:
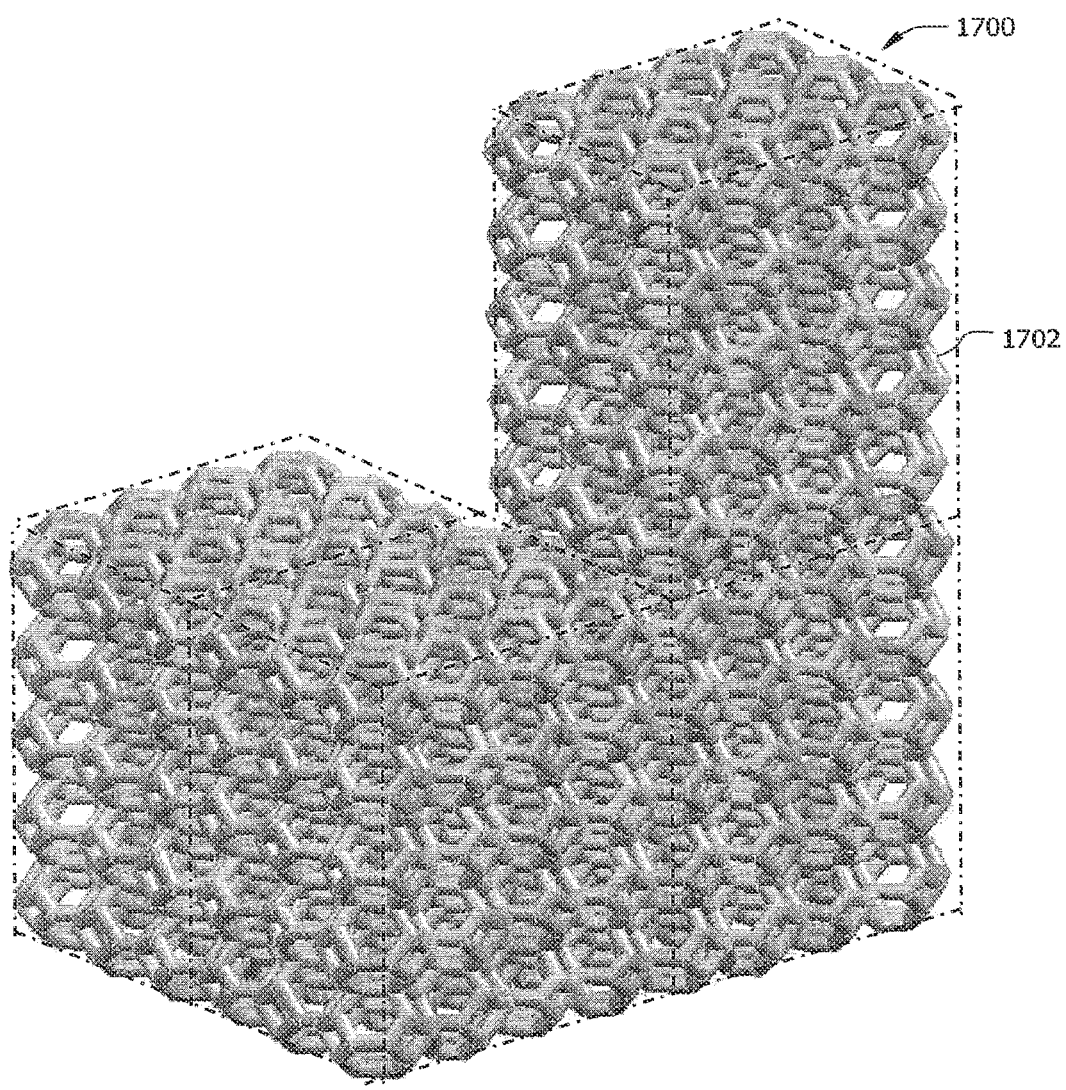
FIG. 17 illustrates one embodiment of a porous structure with four (4) volumes of randomized struts having a 10% randomization limit according to one aspect of the present invention.
Figure 18:
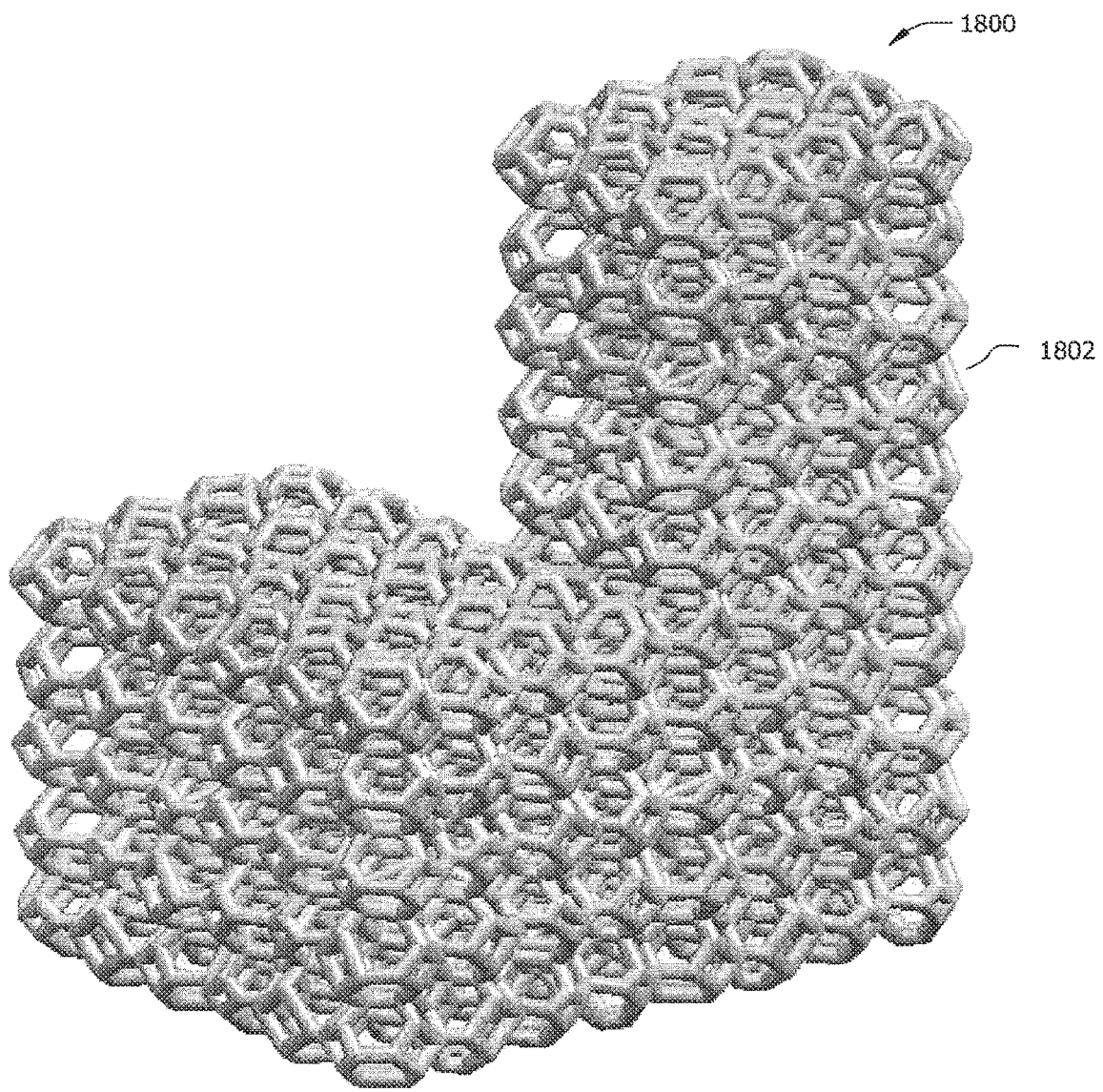
FIG. 18 illustrates one embodiment of a porous structure with four (4) volumes of randomized struts having a 20% randomization limit according to one aspect of the present invention.
Figure 19:
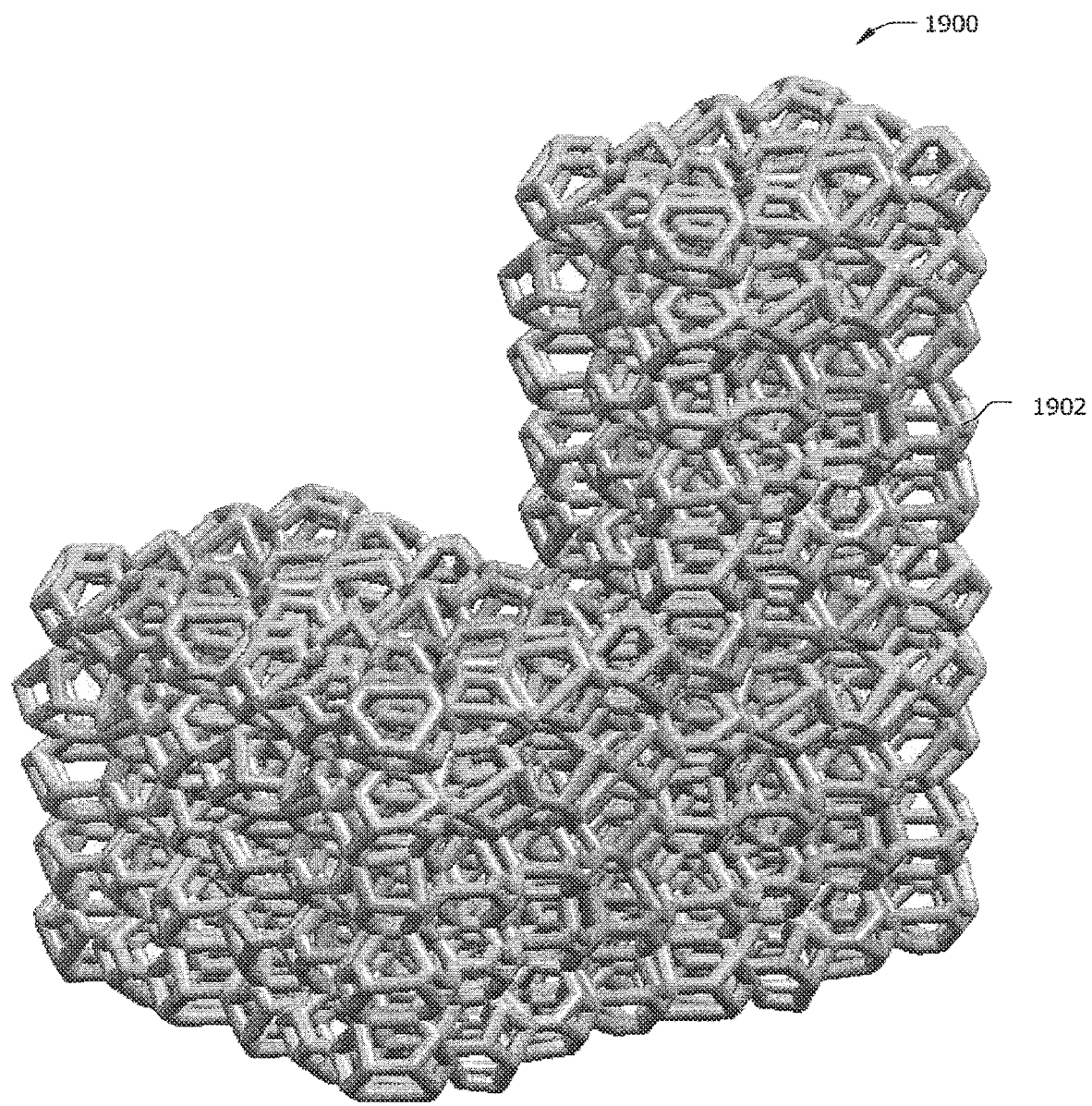
FIG. 19 illustrates one embodiment of a porous structure with four (4) volumes of randomized struts having a 30% randomization limit according to one aspect of the present invention.

In at least the refinements where the volume of randomized seed points are first multiplied and tiled to form a generally shaped scaffold of desired dimensions before the total volume of that scaffold is divided between the randomized seed points, an algorithm to unite the different volumes may not be necessary as process produces a seamlessly divided overall scaffold. In other refinements, however, a Boolean unite algorithm may be used to create a more unified scaffold if necessary. Referring to FIGS. 17-19, after one of the tiles 1702, 1802, 1902 is created, the data for the lines 1204 of the volume 1100 (e.g. FIG. 11) are no longer needed and may be deleted to keep the file size to a minimum. In one variation, the file may be save as a *.prt, or part file, which is the native file format for UNIGRAPHICS™. A para-solid format may also be employed.

In FIG. 17, individual tiles 1702 have struts that have been randomized at a 10% randomization limit. Porous structure 1700 is made up of four identical tiles 1702. Similarly, in FIGS. 18 and 19, tiles 1802 have struts randomized at a 20% randomization limit and tiles 1902 at a 30% randomization limit. While FIGS. 17-19 show porous structures 1700, 1800, and 1900 comprising identical tile volumes, these serve as examples and do not limit the scope of the invention. For instance, in one embodiment, a porous structure can comprise of a combination of tiles that were randomized at limits of 0%, 10%, 20%, 30%, etc. In other refinements, a porous structure can comprise of tiles that have different shapes, and the tiles may or may not have the same randomization limits.

Figure 20:
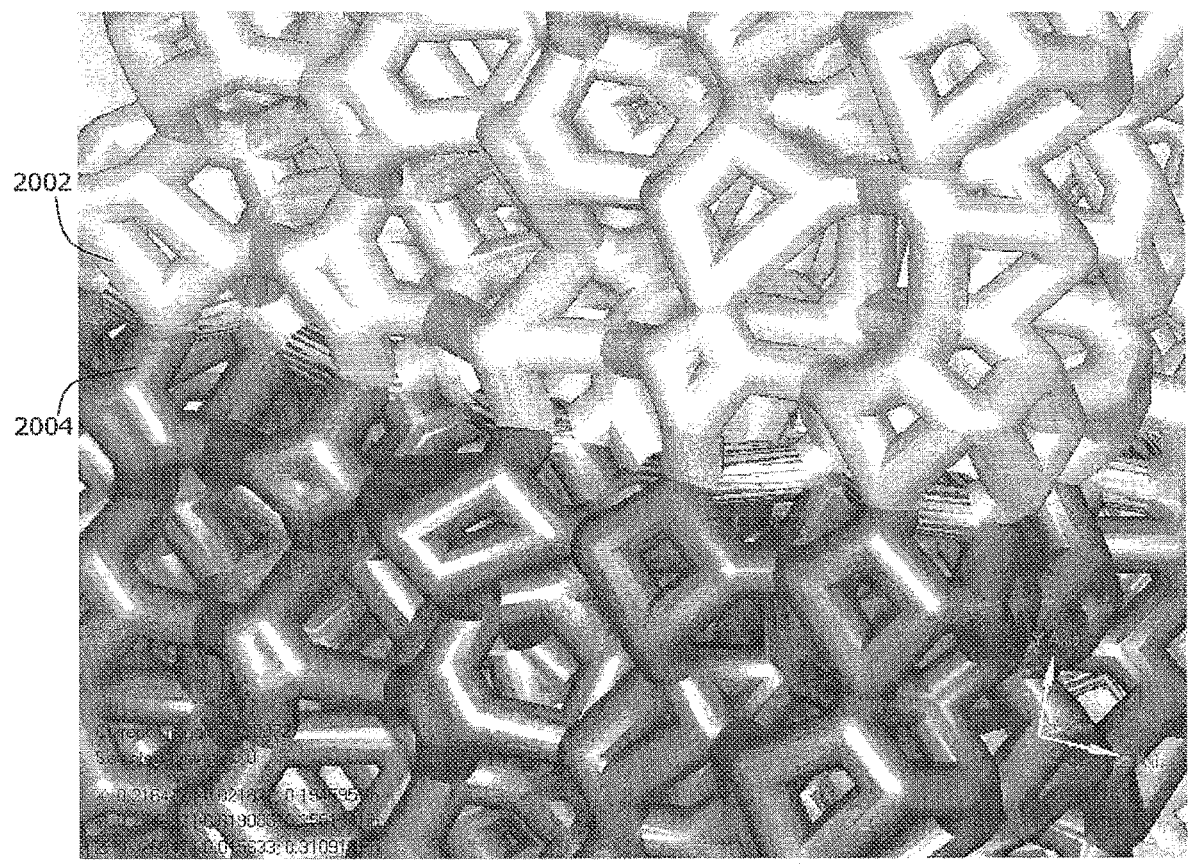
FIG. 20 is a partial view of the porous structure of FIG. 19 illustrating one embodiment of a porous structure having a seamless interface between two or more volumes of randomized struts according to one aspect of the present invention.
Figure 28A:
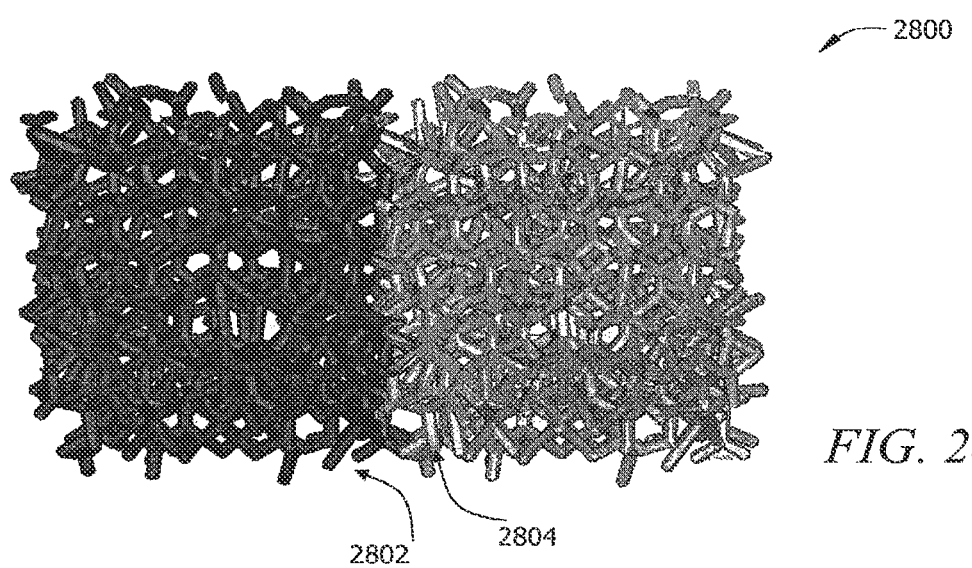
FIGS. 28A-28B illustrate a porous structure according to one aspect of the present invention with two different randomized tiles seamlessly joined together.
Figure 28B:
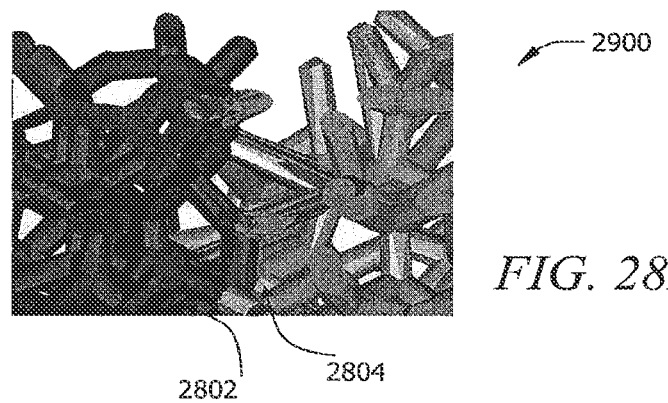

The tiles 1702, 1802, and 1902 may be arranged row by row and stacked with only the outermost struts 1204 overlapping to create any size or shape as illustrated in FIGS. 17-19. The tiles or volumes 1702, 1802, and 1902 may be assembled to create a bulk structure for use at a later time. A Boolean unite algorithm may be used to create the seamless body from two tiles 2002 and 2004 as shown in FIG. 20. As seen, tiles 2002 and 2004 can be substantially identical or tiles 2002 and 2004 can be different shapes and randomization. For example, FIGS. 28A and 28B illustrate an example of a porous structure having two tiles with different maximum pore size. Regardless of the shape or randomization of the tiles, the disclosed methods provide for a seamless interface between the porous tiles. Individual tiles can be exported as a file that can be tiled within a rapid manufacturing machine or software used by such machines. Individual tiles can be interpreted by the machine and then mapped to individual 3-D tiled positions to minimize file size. As will be apparent to those skilled in the art, the 3-D tiles do not have to be laid in a side-by-side fashion as illustrated in FIGS. 17-19. As discussed above, machines may include metal 'selective' laser sintering machines (SLS), electron beam melting machines (EBM), or laser engineered net shaping (LENS™) machines.

Also, many software applications will work to perform the tiling/forming operation. The tiling can be performed in a solid-modeling program like UNIGRAPHICS™, in a program used for advanced NURBS™ and triangulation manipulation such as GEOMAGIC™, in a program dedicated to triangulated file formats like NetFabb, or manually in the *.stl file itself *.stl files are simply a representation of triangulated solids which can be translated and mirrored with any number of bodies. Once the solid has been tiled and manipulated as desired, an *.stl file or the like can be used in rapid-prototype machines. Once the desired structure is defined, it can be exported to a format readable by rapid prototype machines such as *.stl (stereolithography) format. While the specific tiles 1802, 1902, and 2002 disclosed FIGS. 18-20 are rectangular and arrayed accordingly, the disclosed methods apply to a multitude of tiling patterns in three dimensions, such as spherical and cylindrical coordinate tilings. The disclosed methods would be applicable to acetabular cups and stems for example.

Figure 21:
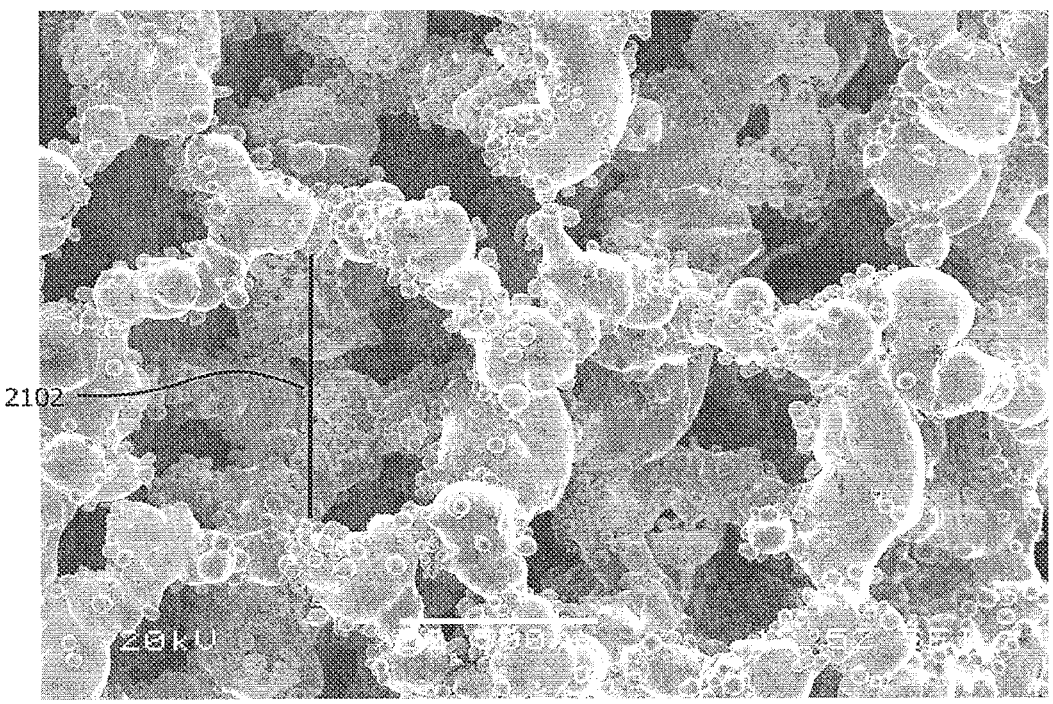
FIG. 21 is a scanning electron microscope (SEM) image of a stainless steel random porous structure made in accordance with one aspect the present invention (image taken at 50×)
Figure 22:
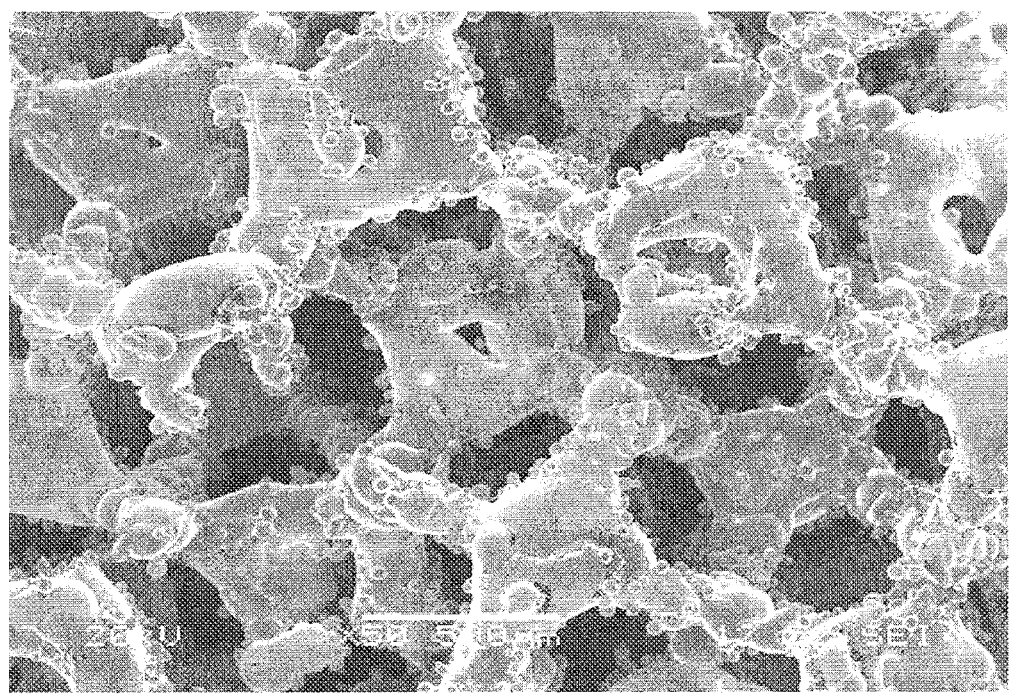
FIG. 22 is another SEM image of a stainless steel random porous structure made in accordance with one aspect the present invention (image taken at 50×)
Figure 23:
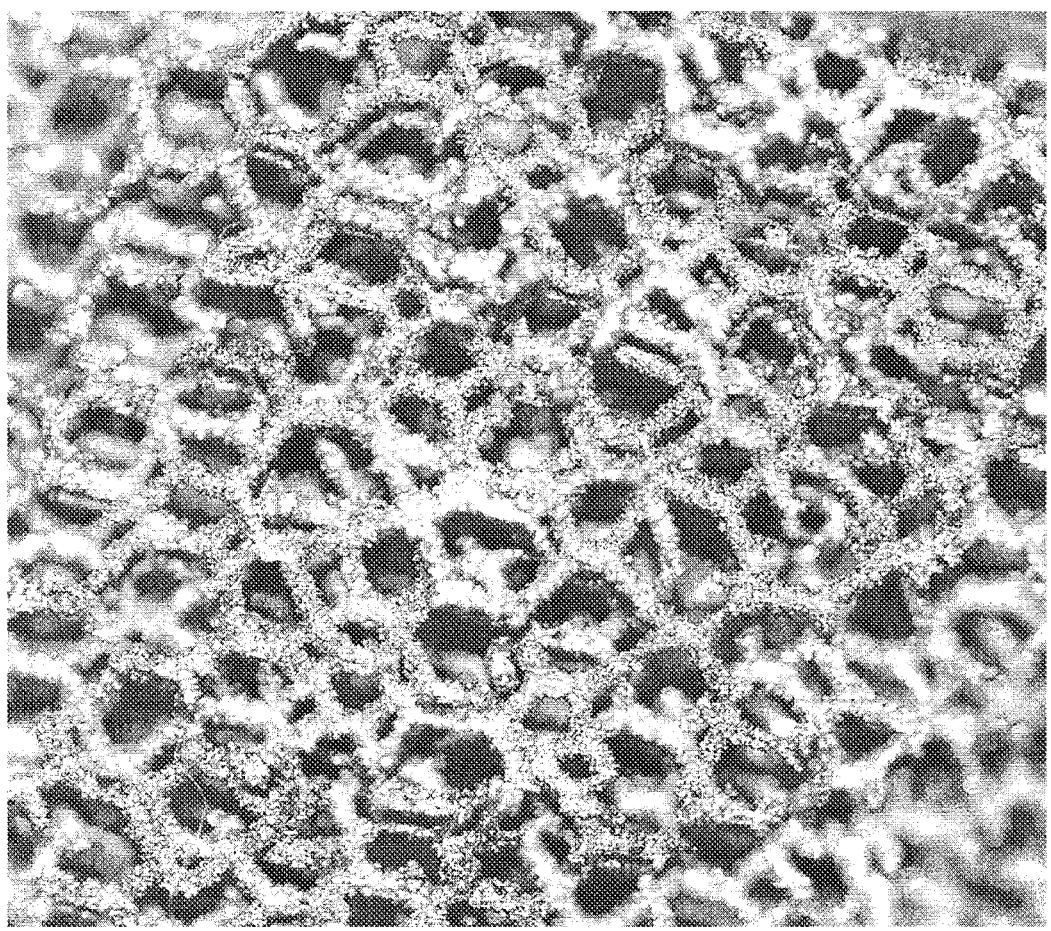
FIGS. 23-25 are photographs of structures fabricated on an EOS™ metal laser sintering machine, employing a 30% randomization limit in accordance with one aspect of the present invention.
Figure 24:
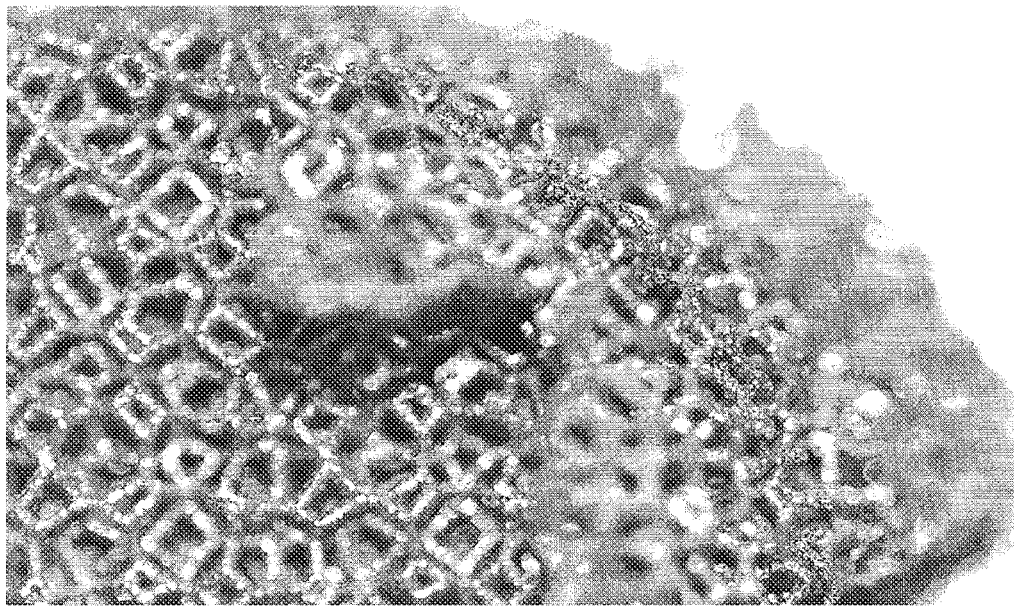
Figure 25:
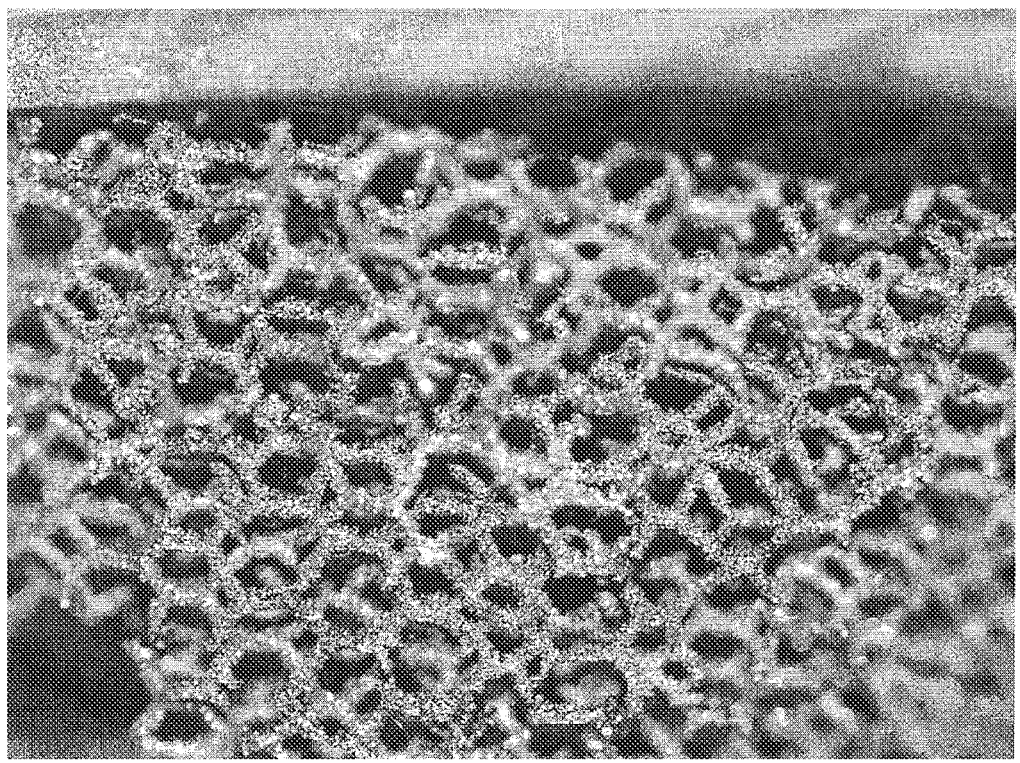

Scanning Electron Microscopy (SEM) photographs of a portion of tiles 1702, 1802, 1902 disclosed FIGS. 17-19 are shown in FIGS. 21-22, and conventional enlarged photographs of tiles 1702, 1802, 1902 disclosed FIGS. 18-20 are shown in FIGS. 23-25. FIG. 24 is a photograph of a curved portion of a metaphyseal cone fabricated on an EOS™ metal laser sintering machine, employing random struts and a 30% randomization limit. FIG. 23 is a photograph of a top portion of the metaphyseal cone shown in FIG. 23. FIG. 25 is a photograph of a cone section of a metaphyseal cone shown in FIGS. 23-24.

Preferred embodiments of porous structures may include 60-85% porosity as known to those skilled in the art. In some embodiments, the average diameter of the pores of the present invention is in the range of 0.01 to 2000 microns. More preferably, the average diameter of the pores is in the range of 50 to 1000 microns. Most preferably, the average diameter of the pores is in the range of 400 to 850 microns. FIG. 21 illustrates one exemplary way the average pore diameter may be measured. The average pore diameter typically is measured by the average diameter of the larger openings captured by an SEM image. In other embodiments, the average diameter 2102 may be measured horizontally or at any desired diagonally position. The average diameter of smaller openings or windows may also be measured.

In a refinement, the average strut thickness for a tile ranges from about 100 μm to about 400 μM. More preferably, the range is from about 180 μm to about 300 μm. In another refinement, the average pore size (MVIL) or fenestration opening diameter ranges from about 200 μm to about 1970 μm, more preferably from 100 μm to 700 μM, and most preferably from 200 μm to 450 μm. Also, the strut thicknesses may be randomized and/or the pore sizes may be randomized.

MVIL refers to Mean Void Intercept Length, which is another way of characterizing the average pore size, particularly in structures where the pore shapes and sizes are not uniform. One generally known definition of MVIL is "measurement grid lines are oriented parallel to the substrate interface. The number of times the lines intercept voids is used with the volume percent void to calculate the mean void intercept length."

Figure 26A:
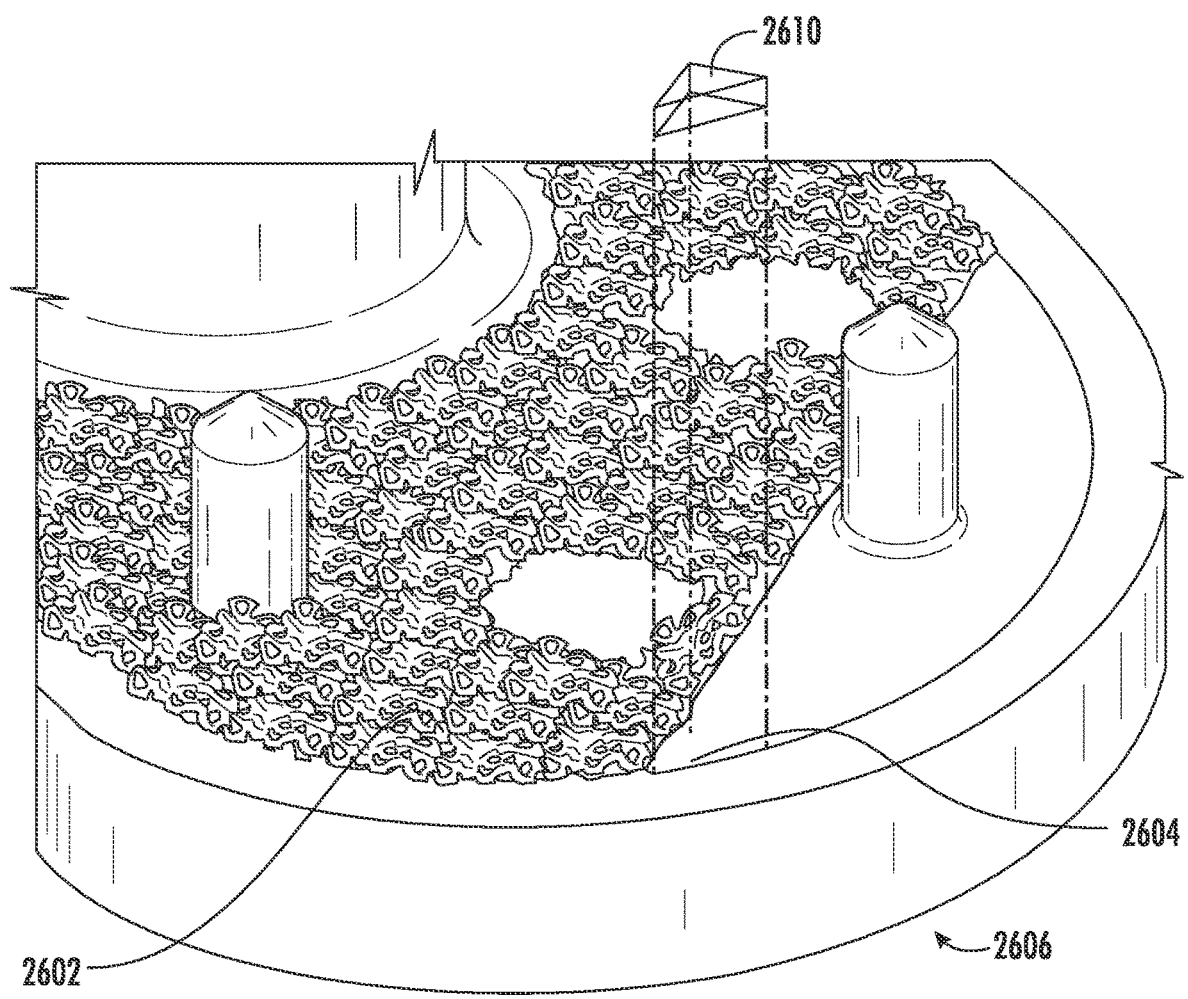
FIGS. 26A-26C illustrates one embodiment of a porous coating being formed from volumes of randomized struts according to one aspect of the present invention.
Figure 26B:
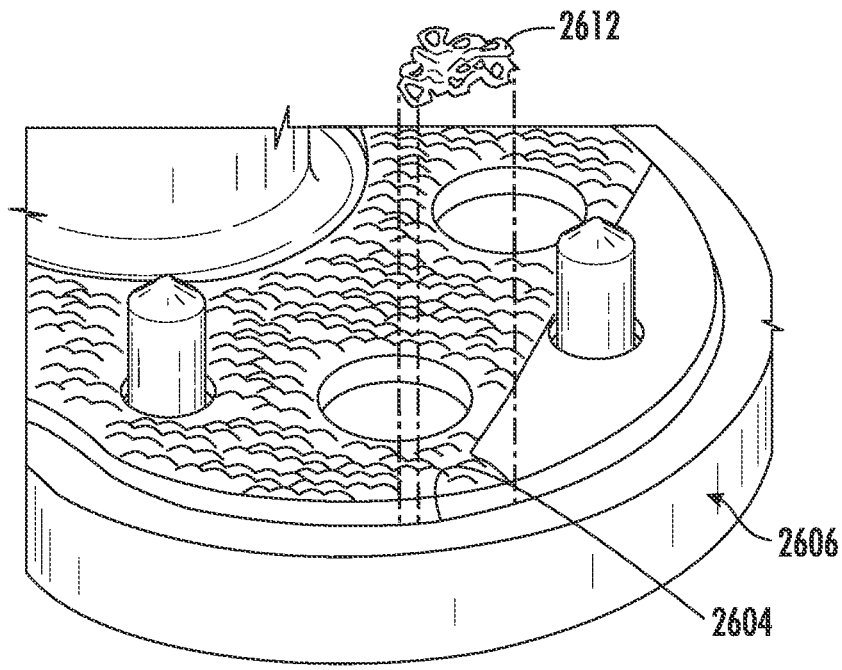
Figure 26C:
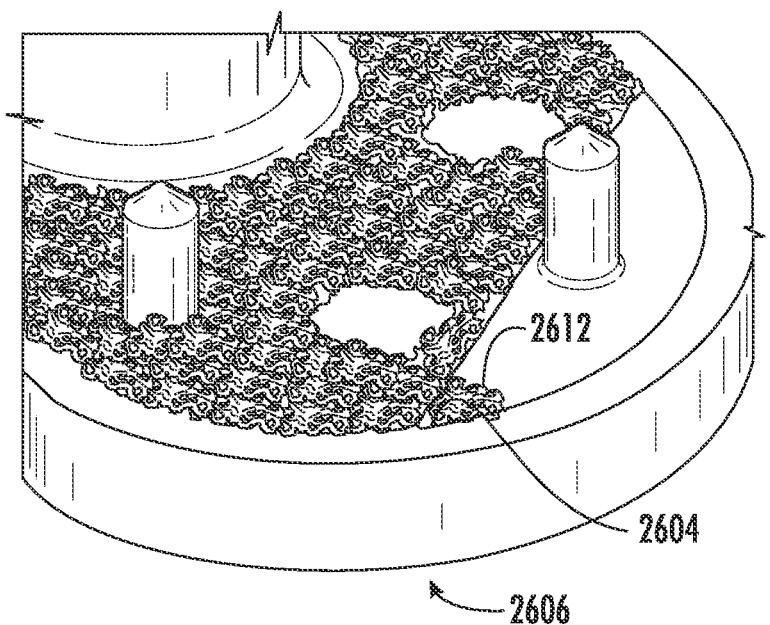
Figure 27:
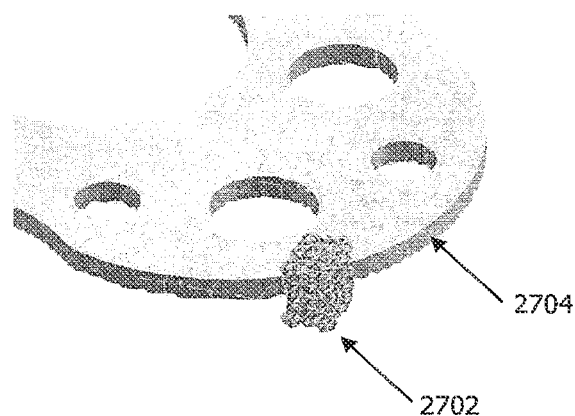
FIG. 27 illustrates one embodiment of a Boolean intersect volume according to one aspect of the present invention.

Boolean-intersect and Boolean unite functions may be employed with base volume of randomized struts 1100 (e.g., FIG. 11) or tile structures like those shown at 1702, 1802, and 1902 disclosed FIGS. 17-19 to apply a coating 2602 on a surface 2604 of an implant or substrate 2606 as illustrated in FIGS. 26A-26C, and the data can be exported to the fabrication machine either with the substrate 2606 data or separately. In FIGS. 26A-26C, the substrate 2606 is a tibial tray that is coated with a plurality of tiles 2702 shown in FIG. 27 to form a porous coating. The desired thickness of the Boolean intersect volume of the coating 2602 is shown at 2704 in FIG. 27. The volume and shape 2610 of the porous material shown in FIG. 26A is used in a Boolean intersect algorithm to convert the larger tile 2702 shown in FIG. 27 to a smaller portion 2612 shown in FIG. 26B for filling the Boolean intersect volume 2610 of FIG. 26A. Thus, using the Boolean intersect algorithm, less than the entire tile 2702 of FIG. 27 may be used to form the portion 2612 of the desired coating geometry or Boolean intersect volume 2610 to create a desired shape. As shown in FIG. 26C, a Boolean unite function may be used to unite the portion 2612 of porous material with surrounding material as the actual coating 2602 is being constructed. Alternately, all of the tiles 1100 (e.g., FIG. 11) or tile structures could be joined together using a Boolean unite and then intersect the joined tiles all at once with the portion 2612 in sub-sections or as a whole. It should be noted that while not shown in the drawings, a base volume of randomized struts, e.g., 1100, may be used to create the portion to be joined 2612, instead of a tile 2702. This may be done such that Boolean intersect volume 2610 is filled with portions of united or un-united portions 2612 of base volume 1100. Strut thicknesses T may be assigned to one or more of the lines 1204 of the tile portions 2612 before or after uniting them. Alternatively, strut thicknesses T may be assigned to one or more of the lines 1204 after the tile portions 2612 are individually or collectively intersected with substrate 2606. In alternative embodiments, Boolean difference or trim operations using planes or sheets can also be used to create the desired shapes, such as volume 2610. In another refinement, before strut thicknesses T may be assigned, a Boolean trim may be performed on the lines 1204 to eliminate certain portions of the lines 1204. As discussed, alternate methods of partitioning the porous volume into its final shape may encompass combinations of intersecting and shaping the solid or precursor lines using trimming sheets. Alternately, this shaping or partitioning by trimming sheets may be performed after slicing or interpreting the solid and porous material into a format readable by a rapid-manufacturing machine.

As mentioned above, FIG. 28A illustrates porous structure 2800 having two tiles 2802 and 2804 joined together seamlessly according to the present disclosure. FIG. 28B is a blown up partial view of the seamless interface between tile 2802 and tile 2804. As demonstrated by FIGS. 28A-28B, the tiles 2802 and 2804 have been designed with a periphery that matches seamlessly on all sides. That is, any permutation of arranging a plurality tiles 2802 and 2804 would result in a porous structure that does not have any discernable seams between the tiles. For example, the interfaces would be seamless between an arrangement having all tiles 2802, or all tiles 2804, or any combination thereof. Yet the inner struts of tile 2802 differ from the struts of tile 2804. For example, tile 2802 has fewer, and therefore, larger pores than tile 2804. The seamless interface was created without the need to manually manipulate the struts to match up or to perform any node matching algorithm.

As demonstrated, the present disclosure provides for the seamless interface between two different scaffold unit tiles without the need to manually manipulate the struts of the two tiles to match up to one another. Instead, in some embodiments, the seamless interface was created by manipulating the negative space, i.e., the space between the struts. The negative space manipulation can be achieved by ensuring that the seed points at the interface between the two tiles, whether substantially identical in shape and randomization or substantially different, correspond to one another. For instance, preferably, there should be only one shared subset of outer seed points at the interface of two tiles. This can be achieved at least by randomizing the outer seed points separate from the inner seed points, limiting the randomization of certain inner seed points, or adding or removing inner seed points. After the negative space is divided to form a scaffold, then the struts can be given a shape and a size to create a seamless porous structure that is made up of different tiles. Preferably, two seed point clouds, whether dissimilar or not, that share a boundary before the scaffold is created will share struts after the scaffold is created.

In view of the above, the present disclosure provides for methods to fabricate a randomized porous structure by manipulating the negative space, i.e., the space between the struts, rather than manipulating the struts themselves for randomization. Accordingly, the methods of the present disclosure allows for time- and cost-effective fabrications of complex porous structure. The present disclosure provides for methods to fabricate original randomized structures, as opposed to a randomized existing structure, that have seamless unions between any connecting units. Consequently, the porous structure created according to the aspects of the present disclosure provide improved strength without requiring the struts to be thicker, as other uniform porous structures may. Further, the randomized structure provides enhanced stress or vibration resistance due to the randomized placement of the struts and their intersections, thereby eliminating planes of fractures that exist in uniform structures where the structures are exposed to shear stress. Additionally, the improved complexity of the porous structures of the present disclosure provides for resemblance of trabecular features and improved porosity. Moreover, the methods of the present disclosure allow for simple and efficient customization of a porous structures with the desired strength, pore distribution, average pore sizes, porosity, etc.

Also, the present disclosure may be used to create and combine a plurality of tiles without randomizing the seed points. The tiles can have substantially identical or substantially different shapes and/or sizes, ranging from simple to complex structure, as long as the tiles have the same or corresponding outer seed points, a seamless interface can be formed when the space is divided. In some embodiments, creating a seamless union between one tile of one shape or size can have a regular distribution of seed points and another tile of another shape and/or size can be done by ensuring the same placement in both tiles of the seed points that most influences the boundary between the tiles, i.e., the outer seed points. For example, it is difficult to create a Weaire-Phelan structure as a tile that is stackable to form a seamless porous structure. The methods described in the present disclosure, however, provide for simple techniques to achieve such tasks and allow for automation of such process via programming of software.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A process for creating a porous structure using a computer-aided apparatus, comprising:
   creating a model of the porous structure;
   converting the model to a format compatible with the computer-aided apparatus;
   providing the converted model to the computer-aided apparatus, the model defining one or more stacked or tiled base volumes of randomized struts;
   controlling the computer-aided apparatus to iteratively deposit successive layers of a material, each successive layer of material creating a cross-section of the porous structure in accordance with the model; and
   controlling the computer-aided apparatus to fuse, melt, re-melt or sinter each successive layer of deposited material by application of energy from an energy source;
   wherein the model is created by defining one or more stacked or tiled base volumes of randomized struts, each strut having an elongated body and a node at each end thereof, each strut being connected to one or more other struts at a node; and
   wherein the location and size of the struts are randomized by dividing each base volume into a plurality of three-dimensional cells defined by a tessellation process applied to a plurality of randomized seed points within each base volume, wherein edges of the three-dimensional cells define the elongated bodies of the struts and vertices of the three-dimensional cells define end nodes of the struts.

2. The process of claim 1, wherein the base volumes are joined together using a Boolean unite function.

3. The process of claim 1 wherein the base volumes have differing properties including one or more of randomization limits, strut shapes and porosities.

4. The process of claim 1 wherein each of the base volumes are created by a process comprising:
   defining a plurality of outer seed points evenly distributed at an outer boundary of the base volume;
   defining a plurality of inner seed points evenly distributed in the interior of the base volume;
   perturbing the locations of the each of the outer and inner seed points a random distance in a random direction; and
   dividing the interior volume of each base volume into a plurality three dimensional cells.

5. The process of claim 4 wherein each base volume is a hexahedron and further wherein outer seed points on opposite sides of the hexahedron are perturbed in the same random distances and random directions.

6. The process of claim 4 wherein a distance between nearest neighboring seed points after perturbation of the inner seed points is limited by a randomization limit.

7. The process of claim 6 wherein the randomization limit is different for inner seed points and outer seed points.

8. The process of claim 4 wherein the model is created by:
creating a plurality of base volumes having divided inner volumes; and
tiling a sufficient number of the base volumes to form the model with desired dimensions.

9. The process of claim 8 wherein dividing the interior volume of each base volume comprises:
applying a Voronoi tessellation to the base volumes to create the plurality of three-dimensional cells having the inner seed points as centroids of each three-dimensional cell;
wherein the edges of each three-dimensional cell define the location of the struts for the model.

10. The process of claim 4 wherein the model is created by:
creating a single base volume having perturbed seed points;
dividing the interior volume of each base volume into a plurality three dimensional cells; and
tiling a sufficient number of identical copies of the single base volume to form the model with desired dimensions.

11. The process of claim 10 wherein the tessellation is a Voronoi tessellation.

12. The process of claim 1 wherein the model further specifies a cross-sectional shape and thickness for each strut.

13. The process of claim 12 wherein the cross-sectional shape and thickness for each strut differs from strut-to-strut.

14. The process of claim 12 wherein the model further specifies a taper angle for each strut.

15. The process of claim 1 wherein each base volume is a plesiohedra.

16. The process of claim 15 wherein each base volume is a convex polyhedral having regular faces.

17. The process of claim 15 wherein each base volume is a convex polyhedral having irregular faces.

18. The process of claim 1 wherein the porous structure is an orthopedic implant.

19. The process of claim 1 wherein the computer-aided apparatus comprises:
a build platform;
a processor;
an energy source; and
software for execution on the processor for controlling the energy source as directed by the model.

* * * * *